(12) United States Patent
von Rege et al.

(10) Patent No.: US 10,472,237 B2
(45) Date of Patent: Nov. 12, 2019

(54) AQUEOUS COMPOSITION AND METHOD OF PRODUCING CHLORINE DIOXIDE USING AQUEOUS COMPOSITION

(71) Applicant: Diversey, Inc., Fort Mill, SC (US)

(72) Inventors: Henry von Rege, Alzey (DE); Ingo Mistele, Mannheim (DE)

(73) Assignee: DIVERSEY, INC., Fort Mill, SC (US)

( * ) Notice: Subject to any disclaimer, the term of this patent is extended or adjusted under 35 U.S.C. 154(b) by 0 days.

(21) Appl. No.: 15/735,230

(22) PCT Filed: Jun. 10, 2016

(86) PCT No.: PCT/US2016/036816
§ 371 (c)(1),
(2) Date: Dec. 11, 2017

(87) PCT Pub. No.: WO2016/201178
PCT Pub. Date: Dec. 15, 2016

(65) Prior Publication Data
US 2018/0179058 A1    Jun. 28, 2018

Related U.S. Application Data

(60) Provisional application No. 62/174,564, filed on Jun. 12, 2015.

(51) Int. Cl.
*C01B 11/02* (2006.01)
*A01N 59/00* (2006.01)
*C02F 1/76* (2006.01)
*C11D 3/48* (2006.01)
*C11D 3/04* (2006.01)

(52) U.S. Cl.
CPC ............ *C01B 11/024* (2013.01); *A01N 59/00* (2013.01); *C02F 1/76* (2013.01); *C11D 3/04* (2013.01); *C11D 3/48* (2013.01)

(58) Field of Classification Search
CPC .............................. C01B 11/024; A01N 59/00
See application file for complete search history.

(56) References Cited

U.S. PATENT DOCUMENTS

| 6,231,830 B1 * | 5/2001 | Madray ................... A61K 8/22 252/187.21 |
| 2003/0203827 A1 | 10/2003 | Cooper et al. |
| 2005/0205259 A1 * | 9/2005 | Powell ................... C09K 8/665 166/300 |
| 2006/0097222 A1 | 5/2006 | Doona et al. |
| 2010/0193734 A1 * | 8/2010 | Doona ................... A61L 2/186 252/187.1 |

OTHER PUBLICATIONS

International Search Report and Written Opinion mailed in PCT/US2016/036816.

* cited by examiner

*Primary Examiner* — Gina C Justice
(74) *Attorney, Agent, or Firm* — Bell & Manning, LLC; N. Meredith Porembski

(57) ABSTRACT

An aqueous composition includes an activator, a chlorite ion source, and water. The aqueous composition is alkaline. The aqueous composition produces chlorine dioxide upon contact with an acid. A method of producing chlorine dioxide includes contacting the aqueous composition with an acid.

20 Claims, 1 Drawing Sheet

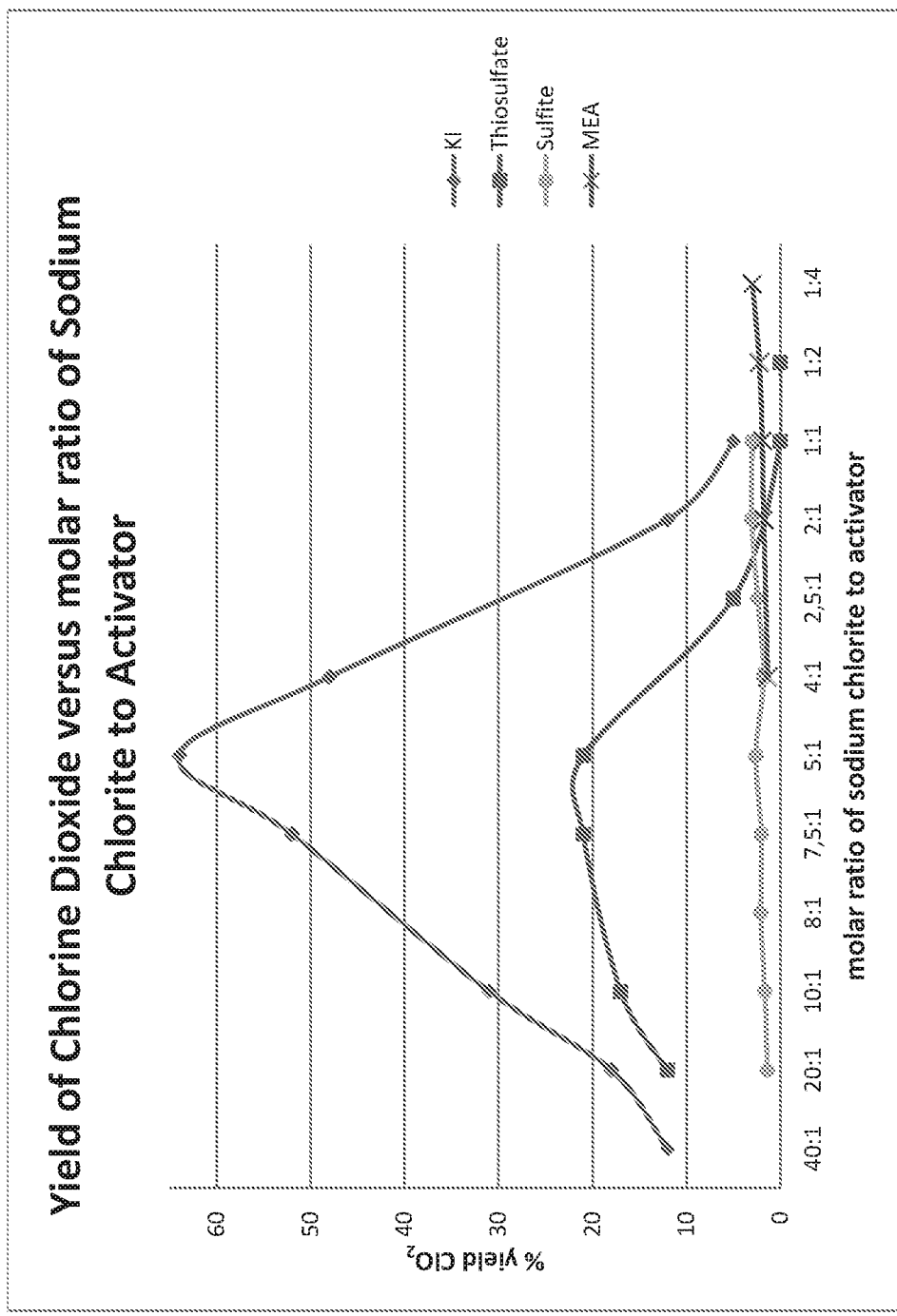

AQUEOUS COMPOSITION AND METHOD OF PRODUCING CHLORINE DIOXIDE USING AQUEOUS COMPOSITION

This application is a National Stage of International Application No. PCT/US2016/036816, filed Jun. 10, 2016, which claims the benefit of U.S. Provisional Patent Application No. 62/174,564, filed Jun. 12, 2015, the contents of which are herein incorporated by reference.

FIELD

The disclosure is related generally to an aqueous composition and a method of producing chlorine dioxide using the aqueous composition.

BACKGROUND

Chlorine dioxide is a potent and useful oxidizing agent that may be used as a disinfectant, biocide, sanitizer, etc. in processes such as water treatment, cleaning, bleaching, etc. Chlorine dioxide is effective against a wide variety of pathogens.

While not wishing to be constrained by any single reaction pathway, one known reaction of sodium chlorite ($NaClO_2$) with hydrochloric acid (HCl) and sodium hypochlorite (NaOCl) produces chlorine dioxide ($ClO_2$), sodium chloride (NaCl), and water ($H_2O$), as follows:

$$2NaClO_2 + 2HCl + NaOCl \rightarrow 2ClO_2 + 3NaCl + H_2O$$

In addition, while not wishing to be constrained by any single reaction pathway, one known reaction of sodium chlorite with hydrochloric acid produces chlorine dioxide, sodium chloride, and water, as follows:

$$5NaClO_2 + 4HCl \rightarrow 4ClO_2 + 5NaCl + 2H_2O$$

Furthermore, while not wishing to be constrained by any single reaction pathway, one known reaction of sodium chlorite with hypochlorous acid (HOCl) produces chlorine dioxide, sodium chloride, and sodium hydroxide, as follows:

$$2NaClO_2 + HOCl \rightarrow 2ClO_2 + NaCl + NaOH$$

Also, while not wishing to be constrained by any single reaction pathway, one known reaction of sodium chlorite with chlorine gas ($Cl_2$) produces chlorine dioxide and sodium chloride, as follows:

$$2NaClO_2 + Cl_2 \rightarrow 2ClO_2 + 2NaCl$$

Chlorine dioxide may exist as a greenish yellow gas at room temperature and possess a characteristic chlorine-like odor. While chlorine dioxide is highly soluble in water. Chlorine dioxide is also highly volatile and may readily migrate out of solution and into the gas phase. Moreover, chlorine dioxide is subject to photochemical decomposition and to chemical decomposition through disproportionation. Therefore, chlorine dioxide solutions may have a relatively short shelf life. When chlorine dioxide is in the gas phase at concentrations exceeding 30% volume in air, at standard temperature and pressure, chlorine dioxide may explosively decompose into chlorine and oxygen. Furthermore, chlorine dioxide is poisonous and is a severe respiratory and eye irritant.

To compensate for the above-noted issues, chlorine dioxide has been produced from relatively stable precursor species at the end use facilities, which has required either a generator to produce chlorine dioxide solutions or a relatively long reaction time to produce chlorine dioxide from generatorless systems.

The generator based systems may use a mechanical or electrical element to facilitate or control the rate of production of chlorine dioxide. Generators may be chemical or electrochemical. Electrochemical generators typically fall into two categories, those that oxidize a chlorite ion and those that reduce a chlorate ion. Chemical based generators typically generate chlorine dioxide by blending high concentrations of sodium chlorite and hydrochloric acid or sulfuric acid. Generator based systems produce relatively high concentrations of chlorine dioxide which may then be diluted to provide solutions including chlorine dioxide at concentrations that are suitable for use. The safety concerns associated with concentrated solutions of chlorine dioxide are well known. Most generators incorporate elaborate safety systems in an attempt to reduce the risk associated with producing, storing and handling these highly concentrated solutions, contributing significantly to the overall cost. The total cost of these generators, including operation and maintenance costs, have limited their application.

Generatorless systems for producing chlorine dioxide are known, however these systems generally require long reaction times to produce solutions of chlorine dioxide. A disadvantage of long reaction times is the risk that a user will not allow adequate formation of chlorine dioxide before using a solution, which results in ineffective microbial kills. Another disadvantage is that the long reaction time prevents quick use.

In addition, a generatorless system may include adding a high concentration of sodium chlorite to an acid solution in a bucket, waiting for the reaction to occur, and adding water to dilute the chlorine dioxide. This procedure can be very dangerous and pose health risks due to the very high concentrations of chlorine dioxide that are produced by the reaction.

As with the concentrated chlorine dioxide solutions produced by the generators, the solutions produced in generatorless systems may require dilution in order to provide a solution having a chlorine dioxide concentration that is suitable for use. The time, safety, and complexity constraints, e.g., the requirement for further dilution processing equipment and control equipment, have limited the application of these systems.

SUMMARY

A first aspect is directed to an aqueous composition comprising:
a reducing agent;
a chlorite ion source; and
water,
wherein the pH of the aqueous composition is at least 11.5, and the composition produces chlorine dioxide upon contact with an acid.

In an embodiment, the reducing agent comprises at least one selected from the group consisting of a reducing sugar, a thiosulfate, a sulfite, a disulfite, urea, thiourea, and dithionites.

In an embodiment, the reducing agent comprises at least one thiosulfate selected from the group consisting of potassium thiosulfate, sodium thiosulfate, calcium thiosulfate, ammonium thiosulfate, and barium thiosulfate.

In an embodiment, the reducing agent comprises at least one sulfite selected from the group consisting of potassium sulfite, sodium sulfite, calcium sulfite, magnesium sulfite, ammonium sulfite, zinc sulfite, silver sulfite, and glycol sulfite.

In an embodiment, the reducing agent comprises sodium thiosulfate, the chlorite ion source comprises sodium chlorite, and the molar ratio of sodium chlorite to sodium thiosulfate in the composition is from 20:1 to 2:1.

A second aspect is directed to an aqueous composition comprising:
at least one selected from the group consisting of iodides and bromides;
a chlorite ion source; and
water,
wherein the pH of the aqueous composition is at least 10.39, and the composition produces chlorine dioxide upon contact with an acid.

In an embodiment, the composition comprises at least one iodide selected from the group consisting of potassium iodide, sodium iodide, lithium iodide, calcium iodide, magnesium iodide, ammonium iodide, potassium triiodide, sodium triiodide, and organo-iodides.

In an embodiment, the composition comprises potassium iodide, the chlorite ion source comprises sodium chlorite, and the molar ratio of sodium chlorite to potassium iodide in the composition is from 40:1 to 1:1.

A third aspect is directed to an aqueous composition comprising:
a catalyst;
a chlorite ion source; and
water,
wherein the pH of the aqueous composition is at least 10.39, and the composition produces chlorine dioxide upon contact with an acid.

In an embodiment, the catalyst comprises potassium iodide.

In an embodiment, the aqueous composition further comprises a separate source of alkalinity.

In an embodiment, the separate source of alkalinity comprises at least one selected from the group consisting of hydroxides, carbonates, silicates, and amines.

In an embodiment, the chlorite ion source comprises at least one selected from the group consisting of alkali metal chlorites and alkaline earth metal chlorites.

In an embodiment, the chlorite ion source comprises at least one selected from the group consisting of sodium chlorite and calcium chlorite.

In an embodiment, the composition produces chlorine dioxide at a concentration of 0.01 to 100 ppm when the composition contacts the acid.

In an embodiment, a method of producing chlorine dioxide comprises contacting the aqueous composition with the acid.

In an embodiment, the method of producing chlorine dioxide further comprises applying chlorine dioxide, produced by contacting the aqueous composition with the acid, in at least one process selected from the group consisting of a disinfection process, a sanitization process, a cleaning process, and a sterilization process.

In an embodiment, a method of producing chlorine dioxide comprises contacting the aqueous composition with at least one selected from the group consisting of an acidic biocide, an acidic detergent, an acidic descaler, an acidic sanitizer, and an acidic disinfectant.

In an embodiment, a method of producing chlorine dioxide comprises contacting the aqueous composition with an acid within equipment during a clean in place process.

In an embodiment, a method of producing chlorine dioxide comprises contacting the aqueous composition with an acid during an open plant cleaning process.

In an embodiment, the acid is in the form of an acidic foam.

In an embodiment, a concentration of the chlorine dioxide produced is 0.01 to 100 ppm.

BRIEF DESCRIPTION OF THE DRAWING

FIG. 1 includes a graph of yield of chlorine dioxide versus molar ratio of sodium chlorite to activator for four types of activators.

DETAILED DESCRIPTION

An aqueous composition may include an activator, a chlorite ion source, and water. The aqueous composition may produce chlorine dioxide upon contact with an acid.

Chlorite ion sources that may be included in the aqueous composition include alkali metal chlorites, an alkaline earth metal chlorites, or mixtures thereof. Examples of alkali metal chlorites that may be included in the aqueous composition include lithium chlorite, sodium chlorite, potassium chlorite, etc. Examples of alkaline earth metal chlorites that may be included in the aqueous composition include beryllium chlorite, barium chlorite, magnesium chlorite, calcium chlorite, etc. In an embodiment, a chlorite ion source includes sodium chlorite.

In an embodiment, the pH of the aqueous composition may be at least 10.39. In an embodiment, the pH of the aqueous composition may be at least 11.5. The alkalinity of the aqueous composition is believed to provide increased stability of chlorite ions in the aqueous composition and may stabilize the activator. The alkalinity of the aqueous composition may also increase the stability of the composition by preventing the undesired formation of chlorine dioxide during storage of the composition.

Alkalinity of the aqueous composition may be provided by, at least, the chlorite ion source. The aqueous composition may also include a separate source of alkalinity. A separate source of alkalinity may include at least one selected from the group consisting of hydroxides, carbonates, silicates, and amines. Examples of amines include monoethanolamine, diethanolamine, triethanolamine, etc. Examples of hydroxides that may be included in the aqueous composition include sodium hydroxide, potassium hydroxide, lithium hydroxide, calcium hydroxide, magnesium hydroxide, etc. Examples of carbonates that may be included in the aqueous composition include sodium carbonate, potassium carbonate, magnesium carbonate, barium carbonate, etc. Examples of silicates that may be included in the aqueous composition include sodium silicate, potassium silicate, magnesium silicate, aluminium silicate, magnesium aluminium silicate, sodium aluminium silicate, calcium silicate, sodium lithium magnesium silicate, etc.

An activator may include a reducing agent and/or a catalyst. Activators that are useful in the composition include iodides, bromides, thiosulfates, dithionites, permanganates, thiourea, urea, percarbonates, peroxodisulfates, sulfites, disulfites, amines, reducing sugars, and mixtures thereof. In embodiment, the activator of the aqueous composition includes a reducing agent. In an embodiment, the activator of the aqueous composition includes a catalyst.

Examples of iodides that may be included in the aqueous composition include potassium iodide, sodium iodide, lithium iodide, calcium iodide, magnesium iodide, ammonium iodide, potassium triiodide, sodium triiodide, organo-iodides, etc. Examples of organo-iodides that may be included in the aqueous composition include short-chain aliphatic iodides, iodoform, iodoacetic acid, iodo silanes, iodo siloxanes, iodoaromatics, etc. Examples of iodoaromatics include iodobenzene, 2-ioiodopyrazole, 6-iodo-2-picolin-5-ol, dobenzoic acid, and iodouracil, etc. In an embodiment, the activator of the aqueous composition includes potassium iodide.

Examples of bromides that may be included in the aqueous composition include potassium bromide, sodium bromide, lithium bromide, calcium bromide, magnesium bromide, ammonium bromide, etc.

Examples of thiosulfates that may be included in the aqueous composition include potassium thiosulfate, sodium thiosulfate, calcium thiosulfate, ammonium thiosulfate, barium thiosulfate, etc. In an embodiment, the aqueous composition includes potassium thiosulfate. In an embodiment, the aqueous composition includes sodium thiosulfate.

Examples of permanganates that may be included in the aqueous composition include potassium permanganate, sodium permanganate, lithium permanganate, calcium permanganate, ammonium permanganate, etc.

Examples of percarbonates that may be included in the aqueous composition include potassium percarbonate, sodium percarbonate, calcium percarbonate, etc. In an embodiment, the aqueous composition includes sodium percarbonate.

Examples of peroxodisulfates that may be included in the aqueous composition include potassium peroxodisulfate, sodium peroxodisulfate, ammonium peroxodisulfate, etc.

Examples of sulfites that may be included in the aqueous composition include potassium sulfite, sodium sulfite, calcium sulfite, magnesium sulfite, ammonium sulfite, zinc sulfite, silver sulfite, glycol sulfite, etc. In an embodiment, the aqueous composition includes sodium sulfite.

Examples of disulfites that are useful in the composition include sodium disulfite and potassium disulfite.

Examples of reducing sugars that are useful in the composition include glucose, glyceraldehyde, galactose, lactose, maltose, etc.

The aqueous composition may further include one or more additives. In embodiments, the composition may include aminotris(methylenephosphonic acid) (ATMP), Armohib 28(TM), 1-hydroxyethane 1,1-diphosphonic acid (HEDP), 2-phosphonobutane-1,2,4-tricarboxylic acid (PBTC), etc., which are believed to be corrosion inhibitors.

Conventional chlorine dioxide generators mix a strong acid with a highly concentrated solution of chlorite ions, which results in a reaction producing a highly concentrated solution of chlorine dioxide. The resulting chlorine dioxide solution may be stored in a day tank where it may be diluted prior to use. A disadvantage of this technology is that the combination of acid with a concentrated solution of chlorite ions increases the potential for a potentially hazardous chlorine dioxide release in the case of a system malfunction. Another disadvantage of conventional chlorine dioxide generators is that the stock chlorine dioxide solution that is produced by these systems has a limited shelf life and must be drained when there is no constant need for chlorine dioxide.

However, the aqueous composition including a chlorite ion source and an activator may be added to an acidic solution in a controlled manner to produce the desired amount of chlorine dioxide on demand in a precise location. The aqueous composition may be contacted with a dilute acid at concentrations typically used for cleaning and descaling in the food and beverage industry. In some embodiments, a dilute acid is 0.01 to 5% by weight of acid, e.g., nitric acid, sulfuric acid, phosphoric acid, citric acid, acetic acid, etc. In embodiments, when the aqueous composition contacts an acid, chlorine dioxide may be produced in concentrations of 0.01 to 100 ppm, 0.1 to 60 ppm, 0.5 to 10 ppm, etc. The aqueous composition may also be contacted with a concentrated acid. The aqueous composition may be contacted with an acidic biocide, an acidic detergent, an acidic descaler, an acidic sanitizer, and an acidic disinfectant.

When adding the aqueous composition to an acid, the activator, e.g. reducing agent or catalyst, may help the reaction to proceed with the conversion of the chlorite ions to chlorine dioxide.

In an embodiment, the aqueous composition includes iodide a catalyst. While not wishing to be constrained by any one reaction pathway, one possible explanation of the role of iodide in the conversion of chlorite ions to chlorine dioxide may be provided by the following equations. The initial oxidation of iodide to iodine may be accompanied by a reduction of chlorite to chloride.

$$\begin{array}{l}(2\ I^- \to I_2 + 2\ e^-) \times 2 \\ \underline{ClO_2^- + 4\ e^- + 4\ H^+ \to Cl^- + 2\ H_2O} \\ 4\ I^- + ClO_2^- + 4\ H^+ \to 2\ I_2 + Cl^- + 2\ H_2O\end{array}$$

Subsequently, the iodine may be reduced back to iodide with a corresponding oxidation of chlorite to chlorine dioxide. As such, the iodide may be considered a catalyst in the disproportionation of chlorite to chloride and chlorine dioxide.

$$\begin{array}{l}(ClO_2^- \to ClO_2 + e^-) \times 2 \\ \underline{I_2 + 2\ e^- \to 2\ I^-} \\ 2\ ClO_2^- + I_2 \to 2\ ClO_2 + 2\ I^-\end{array}$$

The overall reaction may proceed as follows:

$$\begin{array}{l}4\ I^- + ClO_2^- + 4\ H^+ \to 2\ I_2 + Cl^- + 2\ H_2O \\ \underline{(2\ ClO_2^- + I_2 \to 2\ ClO_2 + 2\ I^-) \times 2} \\ 4\ I^- + 5\ ClO_2^- + 4\ H^+ + 2\ I_2 \to 2\ I_2 + Cl^- + 4\ ClO_2 + 4\ I^- + 2\ H_2O\end{array}$$

Simplifying the above equation provides the following classic chlorite disproportionation reaction:

$$5ClO_2^- + 4H^+ \to Cl^- + 4ClO_2 + 2H_2O$$

In an embodiment where the aqueous composition includes potassium iodide as a catalyst and sodium chlorite as a chlorite ion source, a separate source of alkalinity, e.g., sodium hydroxide, may be added to the aqueous composition in order to increase the shelf life of the composition. In a solution including iodide ions and chlorite ions, the chlorite ions may oxidize the iodide ions to iodate. When iodide ions are oxidized to iodate, the ability of the iodide to catalyze the reaction of chlorite ions to chlorine dioxide is reduced and the shelf life of the composition decreases because the iodate does not function as catalyst. However, when sodium hydroxide is added to the liquid composition, the composition is provided with additional alkalinity, the oxidation of the iodide catalyst may be decreased, and the shelf life of the composition may be increased.

An aqueous composition that includes a stable mixture of chlorite ions and a catalyst, and that does not undergo a strong reaction until the composition is contacted with an acid, is desirable.

As noted above, the aqueous composition may produce chlorine dioxide upon contact with an acid. Examples of acids that may be used to produce chlorine dioxide, by contacting the aqueous composition with the acid, include hydrochloric acid, nitric acid, sulfuric acid, phosphoric acid, citric acid, acetic acid, methane sulfonic acid, sulphamic acid, formic acid, glycolic acid, etc.

The aqueous composition may be used in clean in place (CIP) processes for cleaning, sanitizing, disinfecting, etc. of internal surfaces of equipment, e.g. vessels, process lines, heat exchangers, centrifuges, piping, etc., without the need to manually dismantle the equipment. In a CIP processes, cleaning parameters, e.g. time, temperature, chemical energy, mechanical action, etc., may be standardized and automated. A CIP system may include any of tanks, valves, pumps, chemical dosing apparatuses, heat exchangers, steam injectors, steam coils, flow meters, pressure meters, conductivity probes, temperature probes, pH probes, other monitoring devices, a control system, etc. An electronic apparatus such as a programmable logic controller, a microprocessor, computer, etc. may be used as the control system in the CIP processes.

The tanks of a CIP system may be used for storage of fluids for a CIP process, e.g. a tank containing the aqueous composition and a tank containing an acid.

A control system of a CIP system may manage concentration, temperature, flow rate, etc. by controlling the unit components of a CIP system.

A CIP delivery pump may provide a motive force to convey fluids to necessary locations in equipment during CIP processes. A CIP system may include spray devices, e.g. spray balls, high pressure rotary spray heads, positioned inside equipment. The spray devices may distribute CIP process fluids to interior surfaces of the equipment.

For example, the steps of a CIP process may include (1) a pre-rinse to eliminate loose residue in the equipment, (2) an alkaline cleaning step, (3) a water rinse to wash out the alkaline product, (4) an acidic descaling step, (5) a water rinse to wash out the acid product, (6) a terminal disinfecting or sanitizing step, and (7) a final water rinse.

In an embodiment, the aqueous composition may be added to such a CIP process during the acidic descaling step, in order to generate chlorine dioxide by contacting the aqueous composition with an acid present in equipment during the descaling step. By adding the aqueous composition during the descaling step, a large quantity of water may be conserved and a large amount of time may be saved by combining steps (4) and (6), and thus eliminating the need for separate steps (6) and (7).

In addition, a single stage acid CIP process may include feeding an acid into equipment followed by a disinfectant. In an embodiment, the aqueous composition may also be added to an acid in such a single stage CIP process and eliminate the need for an additional disinfectant.

Thus, the aqueous composition may be contacted with an acid that is present within equipment during a CIP process. An acid used in an CIP process may be in the form of a foam or gel cleaner or a formulated acid.

The aqueous composition may also be used in connection with open plant cleaning (OPC) processes for cleaning, sanitizing, disinfecting, etc. of open and exposed surfaces such as process machinery, tables and work areas, utensils, walls, ceilings, floors, etc. OPC processes may be manually operated by a human, semi-automatic, or fully automatic. An aqueous composition being used in an OPC process may be contacted with an acid that is also being used in the OPC process.

Manual OPC processes may use the aqueous composition and an acid for scrubbing of surfaces using brushes, mops, buckets, scrubbing pads, squeegees, etc. Manual OPC processes may also include using the aqueous composition and an acid for soaking of objects in soak tanks.

Semi-automatic OPC processes may include using cleaning systems or equipment that is capable of controlling concentration, application, dispensing etc. of the aqueous composition and an acid. In semi-automatic OPC processes, a step of the process may be performed by a human operator.

Automatic OPC process may include application of the aqueous composition in a fully automated process. An electronic apparatus such as a programmable logic controller, a microprocessor, computer, etc. may control the application and sequencing of the automated OPC process.

When using an acid during an OPC process, e.g. for the removal of inorganic soiling or mineral scaling, the aqueous composition may be combined with the acid already used in the OPC process, in order to also clean, sanitize, disinfect, etc.

In addition, the aqueous composition may be added to an acid that is used for soaking or spray washing. For example, the aqueous composition may be fed to a crate washer, a machine that washes crates that are used for food transport, etc. In a crate washer, a disinfection step may be performed before a final water rinse. If the aqueous composition is added to an acidic step performed in the crate washer, the disinfection step may be omitted, saving processing time and expense. In addition, the aqueous composition may be added to an acidic step performed in a crate washer.

An acid used in an OPC process may be in the form of a foam or gel cleaner or a formulated acid for the intended purpose such as descaling or crate washing. Furthermore, low foaming acid detergents and descalers may be used in an OPC process.

The following describes the preparation and testing of the samples that are listed in Table 1:

Sample 1

An aqueous composition was prepared as follows. A first glass beaker was placed on a scale, and then, 4.5 g (12.44 mmol) of 25% sodium chlorite solution (obtained from Clariant, Germany) was placed in the beaker. Next, 95 ml of deionized water was added to the first beaker. After adding the water, a magnetic stirrer was added to the beaker and the contents of the beaker were stirred. Next, 0.5 g (3.01 mmol) of crystalline potassium iodide was added to the first beaker, and the contents of the beaker were further stirred until the potassium iodide dissolved. At 214 days after the date of preparation of the aqueous composition, the pH of the composition was 11.4.

The aqueous composition was subject to ion chromatography tests, in order to determine the amounts of ions that were present in the composition 220 days after the date of preparation of the composition. The tests were performed using a Metrohm Ion Chromatography system equipped with an A supp7 anionics column. The results are shown in Table 2.

At 245 days after the date of preparation of the aqueous composition, the aqueous composition appeared clear and was tested as follows. 35 g of nitric acid (53% active, technical grade) was mixed with 65 ml of deionized water to produce a standard acid concentrate; and 1 ml of the standard acid concentrate and 98 ml of deionized water were added to a second beaker, in order to produce an acid use solution having a pH of 1.4. An amount of 2 ml of the aqueous composition was added to the acid use solution in the second beaker, in order to produce a chlorine dioxide test solution; and then the contents of the second beaker were mixed for a few seconds.

The chlorine dioxide yield that resulted from the addition of the aqueous composition to the acid use solution was measured using a Hach Lange DR5000, UV spectrometer, as follows. First, a reference spectrum was measured by testing only the acid use solution in the spectrometer at 360 nm. The absorbance of the chlorine dioxide test solution was measured in the spectrometer at 360 nm and at 1 minute, 10 minute, and 30 minute intervals after the time of the addition of the aqueous composition to the acid use solution. The absorbance values are listed in Table 3.

The molar extinction coefficient for chlorine dioxide in water at 360 nm is 1250 liter mol$^{-1}$ cm$^{-1}$. A standard 1 cm cuvette was used for measurement in the spectrometer. And therefore, by including the molar extinction coefficient in the Beer-Lambert equation, and accounting for the 1 cm cuvette, the following is equation is provided:

$$A=1250c$$

The character "c" represents concentration in moles per liter, and the character "A" represents absorbance. Rearranging the equation above provides the following equation:

$$c=A/1250$$

In order to convert the concentration "c" from units of moles per liter to units of ppm, the absorbance "A" was multiplied by 67.5 g/mol (molecular weight of chlorine dioxide) and 1000 mg/g as follows:

$$c=A(67.5)(1000)/1250$$

The simplified equation for calculating the concentration "c" of chlorine dioxide (ppm) in the chlorine dioxide test solution is as follows.

$$c=54A$$

The absorbance values measured at the 1 minute, 10 minute, and 30 minute intervals were multiplied by 54 in order to obtain the concentration of chlorine dioxide in ppm at the intervals, which are listed in Table 3. A percent yield was calculated based on the concentration of sodium chlorite that was present in the aqueous composition versus the concentration of chlorine dioxide that was generated in the chlorine dioxide test solution at the same 1 minute, 10 minute, and 30 minute intervals. The percent yield was calculated as follows. Without intending to be constrained by any one reaction pathway, 5 parts of NaClO$_2$ produce 4 parts of ClO$_2$, according to the following reaction:

$$5ClO_2^- + 4H^+ \rightarrow Cl^- + 4ClO_2 + 2H_2O$$

The aqueous composition of sample 1 included 12.44 mmol of chlorite ions. In order to calculate 100% conversion of NaClO$_2$ to ClO$_2$, 12.44 mmol of NaClO$_2$ is multiplied by 4/5 to provide 9.952 mmol of ClO$_2$. The molecular weight of chlorine dioxide in units of mg/mmol is calculated by multiplying 67.5 g/mol of chlorine dioxide by (1 mol/1000 mmol) and (1000 mg/1 g) to provide 67.5 mg/mmol. The concentration of ClO$_2$ after 100% conversion of NaClO$_2$ to ClO$_2$ is calculated by multiplying 67.5 mg/mmol of chlorine dioxide by 9.952 mmol of ClO$_2$ to provide 671.8 mg in 100 ml (6718 mg/l or ppm). 2% of the aqueous composition of sample 1 was added to the acid use solution to provide 6718 ppm×0.02=134.36 ppm. Therefore, 100% yield is 134.36 ppm and 1% yield is 1.34 ppm. Percent yield values for the 1 minute, 10 minute, and 30 minute intervals were calculated by multiplying the concentration (ppm) of chlorine dioxide at the intervals by 100/134.36, and the percent yield values are listed in Table 3.

Sample 2

An aqueous composition was prepared by combining 90 g (248 mmol) of the of 25% sodium chlorite solution with 10 g (60.2 mmol) potassium iodide. The potassium iodide was slowly added to the sodium chlorite solution while mixing, and it was observed that 5 g of the potassium iodide dissolved. The pH of the aqueous composition was above 12.

Sample 3

An aqueous composition was prepared as follows. A glass beaker was placed on a scale, and then, 4.5 g (12.44 mmol) of 25% sodium chlorite solution and 95.5 ml of deionized water were added to the beaker. After adding the water, a magnetic stirrer was added to the beaker and the contents of the beaker were stirred. At 214 days after preparing the aqueous composition, the pH of the composition was 8.9.

The aqueous composition was subject to ion chromatography tests in the same manner as sample 1, and the results are shown in Table 2. After 245 days following the date of preparation of the aqueous composition, the composition appeared clear and 2 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 4

An aqueous composition was prepared by combining 90 g (248 mmol) of the of 25% sodium chlorite solution used in sample 1 with 10 ml of deionized water. At 214 days after preparing the aqueous composition, the pH of the composition was 12.8.

Sample 5

An aqueous composition was prepared by combining 0.5 g (3.01 mmol) of the potassium iodide with 99.5 ml of deionized water. At 214 days after preparing the aqueous composition, the pH of the composition was 8.1.

Sample 6

An aqueous composition was prepared by combining 10 g (60.2 mmol) of the potassium iodide with 90 ml of deionized water. At 214 days after preparing the aqueous composition, the pH of the composition was 9.3.

Sample 7

An aqueous composition was prepared as follows. A glass beaker was placed on a scale, and then, 9 g (24.88 mmol) of the 25% sodium chlorite solution was placed in the beaker. Next, 90 ml of deionized water was added to the beaker. After adding the water, a magnetic stirrer was added to the beaker and the contents of the beaker were stirred. Next, 1 g (6.02 mmol) of the potassium iodide was added to the beaker, and the contents of the beaker were further stirred until the potassium iodide dissolved. While stirring the contents of the beaker, the pH of the contents of the beaker was 11.7. At 120 days after preparing the composition, the pH of the aqueous composition was 9.9.

The aqueous composition was subject to ion chromatography tests, in order to determine the amounts of ions that were present in the composition 56 and 126 days after the date of preparation of the composition, using the same equipment described in sample 1. The results are shown in Table 2.

35 g of nitric acid (53% active, technical grade) was mixed with 65 ml of deionized water to produce a standard acid concentrate; 1 ml of the standard acid concentrate and 98 ml of deionized water were added to a beaker, in order to produce a 1% acid use solution. At 99 days after the date of preparation of the aqueous composition, an aliquot of the composition was added to the 1% acid use solution, which produced a solution having a yellow color and characteristic smell of chlorine dioxide after 30 minutes.

At 151 days after the preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 7'

An aqueous composition was prepared in the same manner as sample 7, except that the potassium iodide was obtained from Bernd Kraft. The aqueous composition was subject to ion chromatography tests, in order to determine the amounts of ions that were present in the composition 174 days after the date of preparation of the composition. The ion chromatography tests were performed using the same equipment described in sample 1. The results are shown in Table 2.

At 199 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 8

An aqueous composition was prepared as follows. A glass beaker was placed on a scale, and then, 9 g (24.88 mmol) of the 25% sodium chlorite solution was placed in the beaker. Next, 90 ml of deionized water was added to the beaker. After adding the water, a magnetic stirrer was added to the beaker and the contents of the beaker were stirred. Next, 1 g (6.02 mmol) of the potassium iodide was added to the beaker, and the contents of the beaker were further stirred. Next, 1 g (1.7 mmol) of 50% active ATMP (obtained from Italmatch Chemicals) was added to the beaker. Upon addition of the ATMP, the aqueous composition turned brown at the position of addition of the ATMP. The pH of the aqueous composition was 9.8 at the position of addition of the ATMP.

Sample 9

An aqueous composition was prepared by adding 1 g (5.7 mmol) of ascorbic acid obtained from Bernd Kraft to a beaker. Next, 90 ml of deionized water was added to the beaker. The ascorbic acid was neutralized in the beaker by addition of sodium hydroxide solution until a pH of 11 was reached. Next, 9 g (24.88 mmol) of 25% sodium chlorite solution was added to the beaker. Next, 1 g (6.02 mmol) of crystalline potassium iodide was added to the beaker and the contents of the beaker were mixed. The pH of the aqueous composition, during mixing, was 11.2. The aqueous composition produced chlorine dioxide after 30 minutes from the time of mixing the composition. The pH of the aqueous composition was 6.5 after 30 minutes from the time of mixing the composition. The aqueous composition produced chlorine dioxide, without addition of further reactants to the composition, within 24 hours.

Sample 10

An aqueous composition was prepared as follows. A glass beaker was placed on a scale, and then, 9 g (24.88 mmol) of the 25% sodium chlorite solution was placed in the beaker. Next, 90 ml of deionized water was added to the beaker. After adding the water, a magnetic stirrer was added to the beaker and the contents of the beaker were stirred. Next, 1 g (6.02 mmol) of the potassium iodide was added to the beaker, and the contents of the beaker were further stirred until the potassium iodide dissolved. Next, 0.1 g (0.99 mmol) 60% active acetic acid (obtained from Solvent Wistol S.A.) was added, in a dropwise manner to the beaker The aqueous composition turned yellow upon addition of each drop of the acetic acid to the composition, and the composition eventually turned completely brown. The pH of the aqueous composition was 6 after addition of the acetic acid.

Sample 11

An aqueous composition was prepared as follows. 0.04 g (0.65 mmol) of boric acid (obtained from Bernd Kraft) and 0.04 g (0.36 mmol) of sorbic acid were added to a beaker and neutralized by dropwise addition of a 50% sodium hydroxide solution (obtained from Brenntag, Germany). Next, 9 g (24.88 mmol) of the 25% sodium chlorite solution, 90 ml of deionized water, and 1 g (6.02 mmol) of the potassium iodide were added to the beaker, and the contents of the beaker were stirred in order to produce an aqueous composition. While stirring the contents of the beaker, the pH of the contents of the beaker was 11.7. At 120 days after preparation of the composition, the pH of the aqueous composition was 8.9.

At 151 days after the date of preparation of the aqueous composition, the composition included a yellow precipitate, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 12

An aqueous composition was prepared as follows. A glass beaker was placed on a scale, and then, 9 g (24.88 mmol) of the 25% sodium chlorite solution was placed in the beaker. Next, 90 ml of deionized water was added to the beaker. After adding the water, a magnetic stirrer was added to the beaker and the contents of the beaker were stirred. Next, 1 g (6.02 mmol) of the potassium iodide was added to the beaker, and the contents of the beaker were further stirred until the potassium iodide dissolved. Next, 2.0 g (25 mmol) of the 50% sodium hydroxide solution was added to the mixture in the beaker and the contents of the beaker were stirred in order to produce the aqueous composition. While stirring the contents of the beaker, including the sodium hydroxide, the pH of the contents of the beaker was 12.8. The composition appeared colorless at the time of preparation. At 120 days after preparation of the composition, the pH of the composition was 12.8.

The aqueous composition was subject to ion chromatography tests, in order to determine the amounts of ions that were present in the composition 56 and 126 after the date of preparation of the composition, using the same equipment described in sample 1. The results are shown in Table 2.

At 25 days after the date of preparation of the aqueous composition, an aliquot of the composition was added to a 1% solution of Beta VA11 (obtained from Diversey, Inc.), which produced a solution having a yellow color and characteristic smell of chlorine dioxide. At 46 days after the date of preparation of the aqueous composition, an aliquot of the composition was added to a 1% solution of Beta VA11, which produced a solution having a yellow color and characteristic smell of chlorine dioxide.

35 g of nitric acid (53% active, technical grade) was mixed with 65 ml of deionized water to produce a standard acid concentrate; 1 ml of the standard acid concentrate and 98 ml of deionized water were added to a beaker, in order to produce a 1% acid use solution. At 99 days after the date of preparation of the aqueous composition, an aliquot of the composition was added to the 1% acid use solution, which produced a solution having a yellow color and characteristic smell of chlorine dioxide.

At 151 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 12'

Sample 12' was prepared in the same manner as the preparation of sample 12. At 18 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 13

An aqueous composition was prepared as follows. A glass beaker was placed on a scale, and then, 9 g (24.88 mmol) of the 25% sodium chlorite solution was placed in the beaker. Next, 90 ml of deionized water was added to the beaker. After adding the water, a magnetic stirrer was added to the beaker and the contents of the beaker were stirred. Next, 1 g (6.7 mmol) of sodium iodide (obtained from Johnson Matthey et Cie) was added. While stirring the contents of the composition, the pH was 12.8. At 120 days after the date of preparation of the composition, the pH of the composition was 9.

The aqueous composition was subject to ion chromatography tests, in order to determine the amounts of ions that were present in the composition 126 days after the date of preparation of the composition, using the same equipment described in sample 1. The results are shown in Table 2.

At 151 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 14

An aqueous composition was prepared as follows. 1 g (4.8 mmol) of citric acid monohydrate (obtained from Jungbunzlauer) was added to a beaker and neutralized to a pH of 7.4 by addition of 1.2 g (15 mmol) of the 50% sodium hydroxide solution. Next, 9 g (24.88 mmol) of the 25% sodium chlorite solution, 90 ml of deionized water, and 1 g (6.02 mmol) of the potassium iodide were added to the beaker, and the contents of the beaker were stirred in order to produce the aqueous composition. The pH of the contents of the beaker was 11.7 while stirring. At 120 days after the date of preparation of the composition, the pH of the composition was 9.1.

At 151 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 15

An aqueous composition was prepared as follows. First, 9 g (24.88 mmol) of 25% sodium chlorite solution was added to a beaker. Next, 90 ml of deionized water was added to the beaker. Next, 1 g (5.7 mmol) of the ascorbic acid was added to the beaker, which provided a clear solution having a pH of 4.4. Next, 0.6 g (7.5 mmol) of the 50% sodium hydroxide solution was added to the beaker to provide a yellow solution having a pH of 11.0. Next, 1 g (6.02 mmol) of the potassium iodide was added to the beaker and the contents of the beaker were mixed. The pH of the aqueous composition, after mixing the potassium iodide, was 10.7. The aqueous composition produced chlorine dioxide, without addition of further reactants to the composition, within 24 hours.

Sample 16

An aqueous composition was prepared as follows. 1 g (1.67 mmol) ATMP (50% solution) was added to a beaker and neutralized to a pH of 7.6 by addition of 0.6 g (7.5 mmol) of the 50% sodium hydroxide solution. Next, 9 g (24.88 mmol) of the 25% sodium chlorite solution, 90 ml of deionized water, and 1 g (6.02 mmol) of the potassium iodide were added to the beaker, and the contents of the beaker were stirred in order to produce an aqueous composition. The final pH of the composition was 10.4. The aqueous composition turned brown and remained brown, without addition of further reactants to the composition, within 24 hours.

Sample 17

An aqueous composition was prepared as follows. 1 g (5.7 mmol) of the ascorbic acid was added to a beaker and neutralized to a pH of 10.7 by addition of 0.5 g (6.3 mmol) of the 50% sodium hydroxide solution. Next, 9 g (24.88 mmol) of the 25% sodium chlorite solution, 90 ml of deionized water, and 1 g (6.02 mmol) of the potassium iodide were added to the beaker, and the contents of the beaker were stirred in order to produce an aqueous composition. The composition appeared slightly yellow and had a pH of 10.9. The aqueous composition produced chlorine dioxide, without addition of further reactants to the composition, within 24 hours.

Sample 18

An aqueous composition was prepared as follows. 4.5 g (12.44 mmol) of the 25% sodium chlorite solution was added to a beaker, and then 95 ml of deionized water was added to the beaker. After adding the water, a magnetic stirrer was added to the beaker and the contents of the beaker were stirred. Next, 0.5 g (3.01 mmol) of the potassium iodide (all potassium iodide that was included in this sample and the following samples was obtained from Bernd Kraft) was added to the beaker, and the contents of the beaker were further stirred until the potassium iodide dissolved, in order to produce an aqueous composition. The composition appeared colorless at the time of preparation. At 96 days after the date of preparation of the composition, the pH of the composition was 8.9.

The aqueous composition was subject to ion chromatography tests, in order to determine the amounts of ions that were present in the composition 31 and 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

35 g of nitric acid (53% active, technical grade) was mixed with 65 ml of deionized water to produce a standard acid concentrate; 1 ml of the standard acid concentrate and 98 ml of deionized water were added to a beaker, in order to produce a 1% acid use solution. At 75 days after the date of preparation of the aqueous composition, an aliquot of the composition was added to the 1% acid use solution, which did not result in the production of a solution having a yellow color for a period of 24 hours.

At 127 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 19

An aqueous composition was prepared as follows. 4.5 g (12.44 mmol) of the 25% sodium chlorite solution was added to a beaker, and then 94 ml of deionized water was added to the beaker. After adding the water, a magnetic stirrer was added to the beaker and the contents of the beaker were stirred. Next, 0.5 g (3.01 mmol) of potassium iodide (all potassium iodide that was included in this sample and the following samples was obtained from Bernd Kraft) was added to the beaker, and the contents of the beaker were further stirred until the potassium iodide dissolved. Next, 1 g (12.5 mmol) of the 50% sodium hydroxide solution was added to the mixture in the beaker and the contents of the beaker were stirred in order to produce the aqueous composition. The composition appeared colorless at the time of preparation. At 96 days after the date of preparation of the composition, the pH of the composition was 12.8

The aqueous composition was subject to ion chromatography tests, in order to determine the amounts of ions that were present in the composition 31 and 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 20

An aqueous composition was prepared as follows. 4.5 g (12.44 mmol) of the 25% sodium chlorite solution was added to a beaker, and then 92 ml of deionized water was added to the beaker. After adding the water, a magnetic stirrer was added to the beaker and the contents of the beaker were stirred. Next, 0.5 g (3.01 mmol) of the potassium iodide was added to the beaker, and the contents of the beaker were further stirred until the potassium iodide dissolved. Next, 3 g (37.5 mmol) of the 50% sodium hydroxide solution was added to the mixture in the beaker and the contents of the beaker were stirred in order to produce the aqueous composition. The composition appeared colorless at the time of preparation. At 96 days after the date of preparation of the composition, the pH of the composition was 13.

The aqueous composition was subject to an ion chromatography test, in order to determine the amounts of ions that were present in the composition 32 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 21

An aqueous composition was prepared as follows. 4.5 g (12.44 mmol) of the 25% sodium chlorite solution was added to a beaker, and then 90 ml of deionized water was added to the beaker. After adding the water, a magnetic stirrer was added to the beaker and the contents of the beaker were stirred. Next, 0.5 g (3.01 mmol) of the potassium iodide was added to the beaker, and the contents of the beaker were further stirred until the potassium iodide dissolved. Next, 5 g (62.5 mmol) of the 50% sodium hydroxide solution was added to the mixture in the beaker and the contents of the beaker were stirred in order to produce the aqueous composition. At 96 days after the date of preparation of the composition, the pH of the composition was 13.2. The composition appeared colorless at the time of preparation.

The aqueous composition was subject to an ion chromatography test, in order to determine the amounts of ions that were present in the composition 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide after some time. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 22

An aqueous composition was prepared as follows. 4.5 g (12.44 mmol) of the 25% sodium chlorite solution was added to a beaker, and then 94 ml of deionized water was added to the beaker. After adding the water, a magnetic stirrer was added to the beaker and the contents of the beaker were stirred. Next, 1.5 g (9.03 mmol) of the potassium iodide was added to the beaker, and the contents of the beaker were further stirred until the potassium iodide dissolved, in order to produce an aqueous composition. The composition appeared colorless at the time of preparation.

At 1 day after the date of preparation of the aqueous composition, an aliquot of the composition was added to a 1% solution of Beta VA11, which resulted in the production of brown solution.

Sample 23

An aqueous composition was prepared as follows. 4.5 g (12.44 mmol) of the 25% sodium chlorite solution was added to a beaker, and then 91 ml of deionized water was added to the beaker. After adding the water, a magnetic stirrer was added to the beaker and the contents of the beaker were stirred. Next, 1.5 g (9.03 mmol) of the potassium iodide was added to the beaker, and the contents of the beaker were further stirred until the potassium iodide dissolved. Next, 3 g (37.5 mmol) of the 50% sodium hydroxide solution was added to the beaker. At 96 days after the date of preparation of the composition, the pH of the composition was 13.1. The composition appeared colorless at the time of preparation.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which resulted in the production of brown solution. It was unclear whether chlorine dioxide was produced.

A 1% acid use solution was prepared, as in sample 18; and at 75 days after the date of preparation of the aqueous composition, an aliquot of the composition was added to the 1% acid use solution, which resulted in the production of brown solution. It was unclear whether chlorine dioxide was produced.

At 127 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure the absorbances, and the concentrations and yields were calculated therefrom, as in sample 1. The absorbances, concentrations, and yields are listed in Table 3.

Sample 24

An aqueous composition was prepared in the same manner as sample 7, except that the potassium iodide that was included in sample 24 was obtained from Bernd Kraft. The composition appeared colorless at the time of preparation. At 96 days after the date of preparation of the composition, the pH of the composition was 11.7.

The aqueous composition was subject to an ion chromatography test, in order to determine the amounts of ions that were present in the composition 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 25

An aqueous composition was prepared as follows. A glass beaker was placed on a scale, and then, 18 g (49.8 mmol) of the 25% sodium chlorite solution was placed in the beaker. Next, 80 ml of deionized water was added to the beaker. After adding the water, a magnetic stirrer was added to the beaker and the contents of the beaker were stirred. Next, 2 g (12 mmol) of the potassium iodide was added to the beaker, and the contents of the beaker were further stirred until the potassium iodide dissolved. At the time of preparation, the composition appeared slightly yellow, which was apparently caused by the high concentration of sodium chlorite. At 96 days after the date of preparation of the composition, the pH of the composition was 12.

The aqueous composition was subject to an ion chromatography test, in order to determine the amounts of ions that were present in the composition 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 0.5 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 26

An aqueous composition was prepared as follows. A glass beaker was placed on a scale, and then, 9 g (24.88 mmol) of the 25% sodium chlorite solution was placed in the beaker. Next, 88 ml of deionized water was added to the beaker. After adding the water, a magnetic stirrer was added to the beaker and the contents of the beaker were stirred. Next, 3 g (18.06 mmol) of the potassium iodide was added to the beaker, and the contents of the beaker were further stirred until the potassium iodide dissolved. The composition appeared colorless at the time of preparation.

At 1 day after the date of preparation of the aqueous composition, an aliquot of the composition was added to a 1% solution of Beta VA11, which resulted in the production of brown solution.

Sample 27

An aqueous composition was prepared as follows. A glass beaker was placed on a scale, and then, 9 g (24.88 mmol) of the 25% sodium chlorite solution was placed in the beaker. Next, 85 ml of deionized water was added to the beaker. After adding the water, a magnetic stirrer was added to the beaker and the contents of the beaker were stirred. Next, 1 g (6.02 mmol) of the potassium iodide was added to the beaker, and the contents of the beaker were further stirred until the potassium iodide dissolved. Next, 5 g (62.5 mmol) of the 50% sodium hydroxide solution was added to the mixture in the beaker and the contents of the beaker were stirred in order to produce the aqueous composition. The composition appeared colorless at the time of preparation. At 96 days after the date of preparation of the composition, the pH of the composition was 13.2.

The aqueous composition was subject to an ion chromatography test, in order to determine the amounts of ions that were present in the composition 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a faint yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 28

An aqueous composition was prepared as follows. A glass beaker was placed on a scale, and then, 18 g (49.8 mmol) of the 25% sodium chlorite solution was placed in the beaker. Next, 75 ml of deionized water was added to the beaker. After adding the water, a magnetic stirrer was added to the beaker and the contents of the beaker were stirred. Next, 2 g (12.04 mmol) of the potassium iodide was added to the beaker, and the contents of the beaker were further stirred until the potassium iodide dissolved. Next, 5 g (62.5 mmol) of the 50% sodium hydroxide solution was added to the mixture in the beaker and the contents of the beaker were stirred in order to produce the aqueous composition. The composition appeared colorless at the time of preparation. At 96 days after the date of preparation of the composition, the pH of the composition was 13.2.

The aqueous composition was subject to an ion chromatography test, in order to determine the amounts of ions that were present in the composition 101 days after the date of preparation of the composition, using the same equipment described in sample 1. The results are shown in Table 2.

At 1 day after the date of preparation of the aqueous composition, an aliquot of the composition was added to a 1% solution of Beta VA11, which produced a solution having a yellow color and characteristic smell of chlorine dioxide. At 22 days after the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 75 days after the date of preparation of the aqueous composition, an aliquot of the composition was added to the 1% acid use solution, which produced a solution having a yellow color and characteristic smell of chlorine dioxide.

At 127 days after the date of preparation of the aqueous composition, the composition appeared clear, and 0.5 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 29

An aqueous composition was prepared as follows. A glass beaker was placed on a scale, and then, 27 g (74.6 mmol) of 25% sodium chlorite solution was placed in the beaker. Next, 55 ml of deionized water was added to the beaker. After adding the water, a magnetic stirrer was added to the beaker and the contents of the beaker were stirred. Next, 15 g (187.5 mmol) of the 50% sodium hydroxide solution was added to the beaker, and the contents of the beaker were further stirred. Next, 3 g (18.06 mmol) of potassium iodide was added to the beaker and the contents were mixed to produce an aqueous composition. At the time of preparation, the composition appeared slightly yellow, which was apparently caused by the high concentration of sodium chlorite. At 41 days after the preparation of the composition, the pH of the composition was 13.3.

On the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 20 days after the date of preparation of the aqueous composition, an aliquot of the composition was added to the 1% acid use solution, which produced a solution having a yellow color and characteristic smell of chlorine dioxide.

At 72 days after the date of preparation of the aqueous composition, the composition appeared clear, and 0.33 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 30

An aqueous composition was prepared as follows. A glass beaker was placed on a scale, and then, 36 g (99.5 mmol) of 25% sodium chlorite solution was placed in the beaker. Next, 40 ml of deionized water was added to the beaker. After adding the water, a magnetic stirrer was added to the beaker and the contents of the beaker were stirred. Next, 20 g (250 mmol) of the 50% sodium hydroxide solution was added to the beaker, and the contents of the beaker were further stirred. Next, 4 g (24.08 mmol) of potassium iodide was added to the beaker and the contents were mixed to produce an aqueous composition. At the time of preparation, the composition appeared slightly yellow, which was apparently caused by the high concentration of sodium chlorite. At 41 days after the preparation of the composition, the pH of the composition was 13.3.

On the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 20 days after the date of preparation of the aqueous composition, an aliquot of the composition was added to the 1% acid use solution, which produced a solution having a yellow color and characteristic smell of chlorine dioxide.

At 72 days after the date of preparation of the aqueous composition, the composition appeared clear, and 0.25 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 31

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.5 g (4.9 mmol) of sodium bromide was added to the beaker and the contents were mixed to produce an aqueous composition. The composition appeared colorless at the time of preparation. At 41 days after the preparation of the composition, the pH of the composition was 12.8.

On the date of preparation of the aqueous composition, an aliquot of the composition was added to a 1% solution of Beta VA11, which produced a minimal amount of yellow coloration and characteristic smell of chlorine dioxide in the solution.

A 1% acid use solution was prepared, as in sample 18; and at 20 days after the date of preparation of the aqueous composition, an aliquot of the composition was added to the 1% acid use solution, which produced a solution having a yellow color and characteristic smell of chlorine dioxide after 30 minutes.

At 72 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 32

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 0.95 g (11.9 mmol) of the 50% sodium hydroxide solution was added to the beaker, and the contents of the beaker were further stirred. Next, 1.5 g (14.6 mmol) of sodium bromide was added to the beaker and the contents were mixed to produce an aqueous composition. The composition appeared colorless at the time of preparation.

On the date of preparation of the aqueous composition, an aliquot of the composition was added to a 1% solution of Beta VA11, which produced a solution having a yellow color and characteristic smell of chlorine dioxide after more than 30 minutes.

Sample 33

An aqueous composition was prepared as follows. A glass beaker was placed on a scale, and then, 9.5 g (26.3 mmol) of 25% sodium chlorite solution was placed in the beaker. Next, 88 ml of deionized water was added to the beaker. After adding the water, a magnetic stirrer was added to the beaker and the contents of the beaker were stirred. Next, 0.9 g (11.3 mmol) of the 50% sodium hydroxide solution was added to the beaker, and the contents of the beaker were further stirred. Next, 2.5 g (24.3 mmol) of sodium bromide was added to the beaker and the contents were mixed to produce an aqueous composition.

On the date of preparation of the aqueous composition, an aliquot of the composition was added to a 1% solution of Beta VA11, which slowly produced a solution having a yellow color and characteristic smell of chlorine dioxide.

Sample 34

An aqueous composition was prepared as follows. A glass beaker was placed on a scale, and then, 4.5 g (12.44 mmol) of 25% sodium chlorite solution was placed in the beaker. Next, 94.75 ml of deionized water was added to the beaker. After adding the water, a magnetic stirrer was added to the beaker and the contents of the beaker were stirred. Next, 0.25 g (12.5 mmol) of the 50% sodium hydroxide solution was added to the beaker, and the contents of the beaker were further stirred. Next, 0.15 g (0.9 mmol) of potassium iodide and 0.35 g (2.8 mmol) iodine were added to the beaker and the contents were mixed to produce an aqueous composition. The composition appeared yellow at the time of preparation, which was apparently caused by the presence of iodine and potassium triiodide. At 39 days after the preparation of the composition, the pH of the composition was 11.9.

The aqueous composition was subject to an ion chromatography test, in order to determine the amounts of ions that were present in the composition 48 days after the date of preparation of the composition, using the same equipment described in sample 1. The results are shown in Table 2.

A 1% acid use solution was prepared, as in sample 18; and at 18 days after the date of preparation of the aqueous composition, an aliquot of the composition was added to the 1% acid use solution, which produced a solution having a yellow color and characteristic smell of chlorine dioxide.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 35

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 5 g (49 mmol) of sodium bromide was added to the beaker and the contents were mixed to produce an aqueous composition. At 39 days after the preparation of the composition, the pH of the composition was 12.5.

On the date of preparation of the aqueous composition, an aliquot of the composition was added to a 1% solution of Beta VA11, which produced a solution having a yellow color and characteristic smell of chlorine dioxide after more than 30 minutes.

A 1% acid use solution was prepared, as in sample 18; and at 18 days after the date of preparation of the aqueous composition, an aliquot of the composition was added to the 1% acid use solution, which produced a solution having a yellow color and characteristic smell of chlorine dioxide after more than 30 minutes.

The aqueous composition was subject to an ion chromatography test, in order to determine the amounts of ions that were present in the composition 48 days after the date of preparation of the composition, using the same equipment described in sample 1. The results are shown in Table 2.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Upon comparison of samples 31-33 and 35, it was found that aqueous compositions including higher concentrations of sodium bromide provided higher rates of production of chlorine dioxide than the aqueous compositions including lower concentrations of sodium bromide, when aliquots of the compositions were added to the 1% solution of Beta VA11.

Sample 36

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.6 g (2.4 mmol) of sodium thiosulfate pentahydrate (obtained from Esseco) was added to the beaker, and the contents of the beaker were further stirred in order to produce the aqueous composition. At 39 days after the preparation of the aqueous composition, the pH of the composition was 12.5.

On the date of preparation of the aqueous composition, an aliquot of the composition was added to a 1% solution of Beta VA11, which produced a solution having a yellow color and characteristic smell of chlorine dioxide.

A 1% acid use solution was prepared, as in sample 18; and at 18 days after the date of preparation of the aqueous composition, an aliquot of the composition was added to the 1% acid use solution, which produced a solution having a yellow color and characteristic smell of chlorine dioxide.

The aqueous composition was subject to an ion chromatography test, in order to determine the amounts of ions that were present in the composition 48 days after the date of preparation of the composition, using the same equipment described in sample 1. The results are shown in Table 2.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 37

An aqueous composition was prepared as follows. A glass beaker was placed on a scale, and then, 4.5 g (12.44 mmol) of 25% sodium chlorite solution was placed in the beaker. Next, 93 ml of deionized water was added to the beaker. After adding the water, a magnetic stirrer was added to the beaker and the contents of the beaker were stirred. Next, 2 g (19 mmol) of sodium carbonate (Soda Ash Dense obtained from Solvay, Germany) and 0.5 g (3.01 mmol) of potassium iodide was added to the beaker and the contents of the beaker were mixed in order to produce the aqueous composition. At 39 days after the preparation of the composition, the pH of the composition was 11.5.

A 1% acid use solution was prepared, as in sample 18; and at 18 days after the date of preparation of the aqueous composition, an aliquot of the composition was added to the 1% acid use solution, which produced a solution having a yellow color and characteristic smell of chlorine dioxide.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 38

An aqueous composition was prepared as follows. A glass beaker was placed on a scale, and then, 4.5 g (12.44 mmol) of 25% sodium chlorite solution was placed in the beaker. Next, 93 ml of deionized water was added to the beaker. After adding the water, a magnetic stirrer was added to the beaker and the contents of the beaker were stirred. Next, 2 g (9.4 mmol) of sodium silicate pentahydrate (obtained from Brenntag, Germany) and 0.5 g (3.01 mmol) of potassium iodide was added to the beaker and the contents of the beaker were mixed in order to produce the aqueous composition. At 39 days after the preparation of the composition, the pH of the composition was 12.6.

A 1% acid use solution was prepared, as in sample 18; and at 18 days after the date of preparation of the aqueous composition, an aliquot of the composition was added to the 1% acid use solution, which produced a solution having a yellow color and characteristic smell of chlorine dioxide.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 39

An aqueous composition was prepared as follows. A glass beaker was placed on a scale, and then, 4.5 g (12.44 mmol) of 25% sodium chlorite solution was placed in the beaker.

Next, 93.5 ml of deionized water was added to the beaker. After adding the water, a magnetic stirrer was added to the beaker and the contents of the beaker were stirred. Next, 0.8 g (0.5 mmol) of potassium permangante (obtained from AppliChem, Germany) was added to the beaker and the contents of the beaker were mixed in order to produce the aqueous composition.

On the date of preparation of the aqueous composition, an aliquot of the composition was added to a 1% solution of Divosan Uniforce VS44 (obtained from Diversey, Inc.), which produced a solution having a yellow color and a characteristic smell of chlorine dioxide.

A 1% acid use solution was prepared, as in sample 18; and at 18 days after the date of preparation of the aqueous composition, an aliquot of the composition was added to the 1% acid use solution, which did not appear to produce a reaction.

Sample 40

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (13.5 mmol) of amino thiocyanate (obtained from Merck, Germany) was added to the beaker and the contents of the beaker were mixed in order to produce the aqueous composition. Upon preparation, the aqueous composition produced a strong smell of ammonia.

Sample 41

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (16.7 mmol) of urea (obtained from Brenntag, Germany) was added to the beaker and the contents of the beaker were mixed in order to produce the aqueous composition. At 39 days after the preparation of the composition, the pH of the composition was 12.8.

On the date of preparation of the aqueous composition, an aliquot of the composition was added to a 1% solution of Divosan Uniforce VS44, which produced a solution having a yellow color and characteristic smell of chlorine dioxide.

A 1% acid use solution was prepared, as in sample 18; and at 18 days after the date of preparation of the aqueous composition, an aliquot of the composition was added to the 1% acid use solution, which produced a solution including some yellow coloration and characteristic smell of chlorine dioxide after 24 hours.

At 70 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 41

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 1 g (16.7 mmol) of urea was added to the beaker and the contents of the beaker were mixed in order to produce the aqueous composition. The aqueous composition appeared clear at the time of preparation.

At 37 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 42

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (6.4 mmol) of sodium percarbonate (obtained from Acros Organics, Belgium) was added to the beaker and the contents of the beaker were mixed in order to produce the aqueous composition. At 34 days after the preparation of the composition, the pH of the composition was 12.7.

On the date of preparation of the aqueous composition, an aliquot of the composition was added to a 1% solution of Divosan Uniforce VS44, which produced a solution having a yellow color and characteristic smell of chlorine dioxide.

A 1% acid use solution was prepared, as in sample 18; and at 13 days after the date of preparation of the aqueous composition, an aliquot of the composition was added to the 1% acid use solution, which produced a solution including some yellow coloration and characteristic smell of chlorine dioxide after 24 hours.

35 g of nitric acid (53% active, technical grade) was mixed with 65 ml of deionized water to produce a standard acid concentrate; 2 ml of the standard acid concentrate and 98 ml of deionized water were added to a second beaker, in order to produce a 2% acid use solution. At 14 days after the date of preparation of the aqueous composition, an aliquot of the aqueous composition was added to the 2% acid use solution, which produced some yellow coloration in the solution and a characteristic smell of chlorine dioxide after 10 hours.

At 65 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 43

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker.

After adding the water, a magnetic stirrer was added to the beaker and the contents of the beaker were stirred. Next, 1 g (4 mmol) of sodium peroxodisulfate (obtained from Merck, Germany) was added to the beaker and the contents of the beaker were mixed in order to produce the aqueous composition. The composition immediately produced yellow coloration and and a characteristic smell of chlorine dioxide.

Sample 44

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (7.9 mmol) of sodium sulfite (obtained from Merck, Germany) was added to the beaker and the contents of the beaker were mixed in order to produce the aqueous composition. At 34 days after the preparation of the composition, the pH of the composition was 12.8.

On the date of preparation of the aqueous composition, an aliquot of the composition was added to a solution of phosphoric acid, which produced a solution having a yellow color and characteristic smell of chlorine dioxide.

A 1% acid use solution was prepared, as in sample 18; and at 13 days after the date of preparation of the aqueous composition, an aliquot of the composition was added to the 1% acid use solution, which produced a solution including some yellow coloration and characteristic smell of chlorine dioxide after 24 hours.

A 2% acid use solution was prepared as in sample 42; and at 14 days after the date of preparation of the aqueous composition, an aliquot of the aqueous composition was added to the 2% acid use solution, which instantly produced a solution including some yellow coloration and characteristic smell of chlorine dioxide.

The aqueous composition was subject to an ion chromatography test, in order to determine the amounts of ions that were present in the composition 43 days after the date of preparation of the composition, using the same equipment described in sample 1. The results are shown in Table 2.

At 65 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 45

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (5.3 mmol) of sodium disulfite (obtained from Merck, Germany) was added to the beaker and the contents of the beaker were mixed in order to produce the aqueous composition. At 34 days after the preparation of the composition, the pH of the composition was 12.1.

On the date of preparation of the aqueous composition, an aliquot of the composition was added to a 1% solution of Beta VA11, which slowly produced a solution having a yellow color and characteristic smell of chlorine dioxide.

A 1% acid use solution was prepared, as in sample 18; and at 13 days after the date of preparation of the aqueous composition, an aliquot of the composition was added to the 1% acid use solution, which produced a solution including some yellow coloration and characteristic smell of chlorine dioxide after 24 hours.

At 65 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 46

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (10.2 mmol) of potassium thiocyanate (obtained from Merck, Germany) was added to the beaker and the contents of the beaker were mixed in order to produce the aqueous composition.

On the date of preparation of the aqueous composition, an aliquot of the composition was added to a 1% solution of Beta VA11, which did not appear to produce a reaction.

Sample 47

An aqueous composition was prepared as follows. A glass beaker was placed on a scale, and then, 4.5 g (12.44 mmol) of 25% sodium chlorite solution was placed in the beaker. Next, 93.9 ml of deionized water was added to the beaker. After adding the water, a magnetic stirrer was added to the beaker and the contents of the beaker were stirred. Next, 0.1 g (0.6 mmol) of potassium iodide and 0.5 g (4.9 mmol) of sodium bromide were added to the first beaker, and the contents of the beaker were further stirred until the potassium iodide and sodium bromide dissolved. Next, 1 g (12.5 mmol) of the 50% sodium hydroxide solution was added to the mixture in the beaker and the contents of the beaker were stirred in order to produce the aqueous composition. The composition appeared clear 1 day after the date of preparation. At 21 days after the preparation of the composition, the pH of the composition was 12.7.

A 1% acid use solution was prepared, as in sample 18; and 1 day after the date of preparation of the aqueous composition, an aliquot of the composition was added to the 1% acid use solution, which produced a solution including yellow coloration and characteristic smell of chlorine dioxide.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the con-

Sample 48

An aqueous composition was prepared as follows. A glass beaker was placed on a scale, and then, 9 g (24.88 mmol) of 25% sodium chlorite solution was placed in the beaker. Next, 89 ml of deionized water was added to the beaker. After adding the water, a magnetic stirrer was added to the beaker and the contents of the beaker were stirred. Next, 2 g (32.7 mmol) of monoethanolamine (obtained from BASF) was added to the beaker, and the contents of the beaker were further stirred in order to produce the aqueous composition. The composition appeared clear 1 day after the date of preparation. At 21 days after the preparation of the composition, the pH of the composition was 10.5.

A 1% acid use solution was prepared, as in sample 18; and 1 day after the date of preparation of the aqueous composition, an aliquot of the composition was added to the 1% acid use solution, which produced a solution including yellow coloration and characteristic smell of chlorine dioxide after 10 minutes.

At 52 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 48'

Sample 48' was prepared in the same manner as sample 48. At 6 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 49

An aqueous composition was prepared as follows. A glass beaker was placed on a scale, and then, 9 g (24.88 mmol) of 25% sodium chlorite solution was placed in the beaker. Next, 89 ml of deionized water was added to the beaker. After adding the water, a magnetic stirrer was added to the beaker and the contents of the beaker were stirred. Next, 2 g (13.4 mmol) of triethanolamine (obtained from BASF, Germany) was added to the beaker, and the contents of the beaker were further stirred in order to produce the aqueous composition. The composition appeared clear 1 day after the date of preparation. At 21 days after the preparation of the composition, the pH of the composition was 8.5.

A 1% acid use solution was prepared, as in sample 18; and 1 day after the date of preparation of the aqueous composition, an aliquot of the composition was added to the 1% acid use solution, which produced a solution including yellow coloration and characteristic smell of chlorine dioxide after 10 minutes.

At 52 days after the date of preparation of the aqueous composition, the composition appeared clear, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 50

An aqueous composition was prepared as follows. A glass beaker was placed on a scale, and then, 4.5 g (12.44 mmol) of 25% sodium chlorite solution was placed in the beaker. Next, 93 ml of deionized water was added to the beaker. After adding the water, a magnetic stirrer was added to the beaker and the contents of the beaker were stirred. Next, 2 g (32.7 mmol) of monoethanolamine and 0.5 g (3.01 mmol) of potassium iodide were added to the beaker, and the contents of the beaker were further stirred in order to produce the aqueous composition. The composition appeared clear 1 day after the date of preparation. At 21 days after the preparation of the composition, the pH of the composition was 10.5.

A 1% acid use solution was prepared, as in sample 18; and 1 day after the date of preparation of the aqueous composition, an aliquot of the composition was added to the 1% acid use solution, which produced a solution including yellow coloration and characteristic smell of chlorine dioxide.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 51

An aqueous composition was prepared as follows. A glass beaker was placed on a scale, and then, 4.5 g (12.44 mmol) of 25% sodium chlorite solution was placed in the beaker. Next, 95.2 ml of deionized water was added to the beaker. After adding the water, a magnetic stirrer was added to the beaker and the contents of the beaker were stirred. Next, 0.3 g (32.7 mmol) of sodium thiosulfate was added to the beaker, and the contents of the beaker were further stirred in order to produce the aqueous composition. The composition appeared clear, but the composition reacted suddenly after twenty hours had passed since the time of preparation of the composition.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

Sample 51'

An aqueous composition was prepared in the same manner as sample 51 and was stored in a closed glass container.

Sample 52

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 1 g (9.4 mmol) of sodium carbonate was added to the beaker, and the contents of the beaker were further stirred in order to produce the aqueous composition. The composition appeared clear 1 day after the date of preparation. At 21 days after the preparation of the composition, the pH of the composition was 10.9.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 53

An aqueous composition was prepared as follows. A glass beaker was placed on a scale, and then, 4.5 g (12.44 mmol) of 25% sodium chlorite solution was placed in the beaker. Next, 92.5 ml of deionized water was added to the beaker. After adding the water, a magnetic stirrer was added to the beaker and the contents of the beaker were stirred. Next, 3 g (50 mmol) of urea was added to the beaker, and the contents of the beaker were further stirred in order to produce the aqueous composition. The composition appeared clear 1 day after the date of preparation. At 21 days after the preparation of the composition, the pH of the composition was 9.8.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 54

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g (13 mmol) of sodium percarbonate was added to the beaker, and the contents of the beaker were further stirred in order to produce the aqueous composition. The composition appeared clear 1 day after the date of preparation. At 21 days after the preparation of the composition, the pH of the composition was 10.3.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 55

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (4.2 mmol) of sodium peroxodisulfate was added to the beaker, and the contents of the beaker were further stirred in order to produce the aqueous composition. The composition immediately produced yellow coloration and a characteristic smell of chlorine dioxide.

Sample 56

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g (16 mmol) of sodium sulfite was added to the beaker, and the contents of the beaker were further stirred in order to produce the aqueous composition. The composition appeared clear 1 day after the date of preparation. At 21 days after the preparation of the composition, the pH of the composition was 9.5.

The aqueous composition was subject to an ion chromatography test, in order to determine the amounts of ions that were present in the composition 35 days after the date of preparation of the composition, using the same equipment described in sample 1. The results are shown in Table 2.

A 1% acid use solution was prepared, as in sample 18; and 1 day after the date of preparation of the aqueous composition, an aliquot of the composition was added to the 1% acid use solution, which produced a solution including yellow coloration and characteristic smell of chlorine dioxide after 15 minutes.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the con- Sample 51' turned yellow and produced characteristic smell of chlorine dioxide 5 minutes after opening the glass container.

Sample 56'

Sample 56' was prepared in the same manner as sample 56.

At 6 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 57

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g of Rewocid® WK 30 (obtained from Evonik Industries AG, Nutrition & Care, Germany) containing N-Alkyl aminopropyl glycine was added to the beaker, and the contents of the beaker were further stirred in order to produce the aqueous composition. The composition appeared clear 1 day after the date of preparation. At 21 days after the preparation of the composition, the pH of the composition was 7.5.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition had a turbid and white appearance, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 58

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g of Trilon® BX liquid (obtained from BASF) containing 40% ethylenediaminetetraacetic acid was added to the beaker, and the contents of the beaker were further stirred in order to produce the aqueous composition. The composition appeared clear 1 day after the date of preparation. At 21 days after the preparation of the composition, the pH of the composition was 10.4.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 59

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g of Trilon® M liquid (obtained from BASF) containing 40% methylglycinediacetic acid was added to the beaker, and the contents of the beaker were further stirred in order to produce the aqueous composition. The composition appeared clear 1 day after the date of preparation. At 21 days after the preparation of the composition, the pH of the composition was 10.7.

A 1% acid use solution was prepared, as in sample 18; and 1 day after the date of preparation of the aqueous composition, an aliquot of the composition was added to the 1% acid use solution, which did not appear to cause a reaction.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 60

An aqueous composition was prepared as follows. A glass beaker was placed on a scale, and then, 4.5 g (12.44 mmol) of 25% sodium chlorite solution was placed in the beaker. Next, 94.2 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.28 g (1.13 mmol) of sodium thiosulfate pentahydrate was added to the beaker, and the contents of the beaker were further stirred in order to produce the aqueous composition. The composition appeared clear 1 day after the date of preparation. At 21 days after the preparation of the composition, the pH of the composition was 12.5.

A 1% acid use solution was prepared, as in sample 18; and 1 day after the date of preparation of the aqueous composition, an aliquot of the composition was added to the 1% acid use solution, which produced a solution having a yellow color and characteristic smell of chlorine dioxide.

The aqueous composition was subject to an ion chromatography test, in order to determine the amounts of ions that were present in the composition 35 days after the date of preparation of the composition, using the same equipment described in sample 1. The results are shown in Table 2.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 61

An aqueous composition was prepared as follows. A glass beaker was placed on a scale, and then, 4.5 g (12.44 mmol) of 25% sodium chlorite solution was placed in the beaker. Next, 93 ml of deionized water was added to the beaker. After adding the water, a magnetic stirrer was added to the beaker and the contents of the beaker were stirred. Next, 0.56 g (2.26 mmol) of sodium thiosulfate pentahydrate and 2 g (13 mmol) of triethanolamine were added to the beaker, and the contents of the beaker were further stirred in order to produce the aqueous composition. The composition appeared clear 1 day after the date of preparation. At 21 days after the preparation of the composition, the pH of the composition was 8.8.

A 1% acid use solution was prepared, as in sample 18; and 1 day after the date of preparation of the aqueous composition, an aliquot of the composition was added to the 1% acid use solution, which produced a solution having a yellow color and characteristic smell of chlorine dioxide.

The aqueous composition was subject to an ion chromatography test, in order to determine the amounts of ions that were present in the composition 35 days after the date of preparation of the composition, using the same equipment described in sample 1. The results are shown in Table 2.

At 52 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 62

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 2 g (14 mmol) of anhydrous sodium sulfate was added to the beaker, and the contents of the beaker were further stirred in order to produce the aqueous composition. The composition appeared clear at the time of preparation. At 12 days after the preparation of the composition, the pH of the composition was 11.1.

A 1% acid use solution was prepared, as in sample 18; and on the date of preparation of the aqueous composition, an aliquot of the composition was added to the 1% acid use solution, which produced a solution including some yellow coloration and characteristic smell of chlorine dioxide after 30 minutes.

At 43 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 63

An aqueous composition was prepared as follows. A glass beaker was placed on a scale, and then, 4.5 g (12.44 mmol) of 25% sodium chlorite solution was placed in the beaker. Next, 91.5 ml of deionized water was added to the beaker. After adding the water, a magnetic stirrer was added to the beaker and the contents of the beaker were stirred. Next, 4 g (31.7 mmol) of sodium sulfite was added to the beaker, and the contents of the beaker were further stirred in order to produce the aqueous composition. The composition appeared clear at the time of preparation. At 12 days after the preparation of the composition, the pH of the composition was 11.4.

A 1% acid use solution was prepared, as in sample 18; and on the date of preparation of the aqueous composition, an aliquot of the composition was added to the 1% acid use solution, which did not appear to produce a reaction.

At 43 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 64

An aqueous composition was prepared as follows. A glass beaker was placed on a scale, and then, 4.5 g (12.44 mmol) of 25% sodium chlorite solution was placed in the beaker. Next, 90 ml of deionized water was added to the beaker. After adding the water, a magnetic stirrer was added to the beaker and the contents of the beaker were stirred. Next, 5 g (32 mmol) of sodium percarbonate was added to the beaker, and the contents of the beaker were further stirred in order to produce the aqueous composition. The composition appeared clear and included many gas bubbles at the time of preparation. At 12 days after the preparation of the composition, the pH of the composition was 10.9.

A 1% acid use solution was prepared, as in sample 18; and on the date of preparation of the aqueous composition, an aliquot of the composition was added to the 1% acid use solution, which produced a solution including a light yellow color and characteristic smell of chlorine dioxide.

At 43 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 65

An aqueous composition was prepared as follows. A glass beaker was placed on a scale, and then, 2 g (5.5 mmol) of 25% sodium chlorite solution was placed in the beaker. Next, 97.7 ml of deionized water was added to the beaker. After adding the water, a magnetic stirrer was added to the beaker and the contents of the beaker were stirred. Next, 0.25 g (1.5 mmol) of potassium iodide was added to the beaker, and the contents of the beaker were further stirred in order to produce the aqueous composition. The composition appeared clear at the time of preparation. At 7 days after the preparation of the composition, the pH of the composition was 9.7.

At 38 days after the date of preparation of the aqueous composition, the composition appeared clear, and 4 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 66

An aqueous composition was prepared as follows. A glass beaker was placed on a scale, and then, 4 g (11 mmol) of 25% sodium chlorite solution was placed in the beaker. Next, 95.5 ml of deionized water was added to the beaker. After adding the water, a magnetic stirrer was added to the beaker and the contents of the beaker were stirred. Next, 0.4 g (2.4 mmol) of potassium iodide was added to the beaker, and the contents of the beaker were further stirred in order to produce the aqueous composition. The composition appeared clear at the time of preparation. At 7 days after the preparation of the composition, the pH of the composition was 10.4.

At 38 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 67

An aqueous composition was prepared as follows. A glass beaker was placed on a scale, and then, 9 g (24.88 mmol) of 25% sodium chlorite solution was placed in the beaker. Next, 89 ml of deionized water was added to the beaker. After adding the water, a magnetic stirrer was added to the beaker and the contents of the beaker were stirred. Next, 1 g (6 mmol) of potassium iodide and 1 g (6.3 mmol) of calcium acetate were added to the beaker, and the contents of the beaker were further stirred in order to produce the aqueous composition. A precipitate appeared in the composition. At 7 days after the preparation of the composition, the pH of the composition was 11.3.

At 38 days after the date of preparation of the aqueous composition, the composition included a crystalline precipitate, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 68

An aqueous composition was prepared as follows. A glass beaker was placed on a scale, and then, 9 g (24.88 mmol) of 25% sodium chlorite solution was placed in the beaker. Next, 89 ml of deionized water was added to the beaker. After adding the water, a magnetic stirrer was added to the beaker and the contents of the beaker were stirred. Next, 1 g (6 mmol) of potassium iodide and 1 g (2.6 mmol) of borate (obtained by dosing the boric acid into a caustic solution) were added to the beaker, and the contents of the beaker were further stirred in order to produce the aqueous composition. The composition appeared yellow at the time of preparation. At 7 days after the preparation of the composition, the pH of the composition was 9.3.

At 38 days after the date of preparation of the aqueous composition, the composition included a small amount of crystalline precipitate, and 1 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 69

An aqueous composition was prepared as follows. A glass beaker was placed on a scale, and then, 36 g (99.5 mmol) of 25% sodium chlorite solution was placed in the beaker. Next, 10 ml of deionized water was added to the beaker. After adding the water, a magnetic stirrer was added to the beaker and the contents of the beaker were stirred. Next, 4 g (24 mmol) of potassium iodide was added to the beaker, and the contents of the beaker were further stirred in order to produce the aqueous composition. At the time of preparation, the composition appeared yellow, which was apparently caused by the high concentration of sodium chlorite. At 7 days after the preparation of the composition, the pH of the composition was 11.3.

The aqueous composition was subject to an ion chromatography test, in order to determine the amounts of ions that were present in the composition 22 days after the date of preparation of the composition, using the same equipment described in sample 1. The results are shown in Table 2.

At 38 days after the date of preparation of the aqueous composition, the composition included a crystalline precipitate, and 0.25 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 70

An aqueous composition was prepared as follows. A glass beaker was placed on a scale, and then, 22.5 g (62.2 mmol) of 25% sodium chlorite solution was placed in the beaker. Next, 20 ml of deionized water was added to the beaker. After adding the water, a magnetic stirrer was added to the beaker and the contents of the beaker were stirred. Next, 5 g (62.5 mmol) of the 50% sodium hydroxide solution was added to the beaker, and the contents of the beaker were further stirred. Next, 2.5 g (15 mmol) of potassium iodide was added to the beaker and the contents were mixed to produce an aqueous composition. At the time of preparation, the potassium iodide was soluble in the aqueous composition. At 7 days after the preparation of the composition, the pH of the composition was 13.3.

At 38 days after the date of preparation of the aqueous composition, the composition included a crystalline precipitate, and 0.4 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 71

An aqueous composition was prepared as follows. A glass beaker was placed on a scale, and then, 27 g (74.6 mmol) of 25% sodium chlorite solution was placed in the beaker. Next, 14 ml of deionized water was added to the beaker. After adding the water, a magnetic stirrer was added to the beaker and the contents of the beaker were stirred. Next, 6 g (62.5 mmol) of the 50% sodium hydroxide solution was added to the beaker, and the contents of the beaker were further stirred. Next, 3 g (18 mmol) of potassium iodide was added to the beaker and the contents were mixed to produce an aqueous composition. At the time of preparation, the potassium iodide was soluble in the aqueous composition. At 7 days after the preparation of the composition, the pH of the composition was 13.3.

At 38 days after the date of preparation of the aqueous composition, the composition included a crystalline precipitate, and 0.33 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 72

An aqueous composition was prepared as follows. A glass beaker was placed on a scale, and then, 31.5 g (87.1 mmol) of 25% sodium chlorite solution was placed in the beaker. Next, 8 ml of deionized water was added to the beaker. After adding the water, a magnetic stirrer was added to the beaker and the contents of the beaker were stirred. Next, 7 g (87.5 mmol) of the 50% sodium hydroxide solution was added to the beaker, and the contents of the beaker were further stirred. Next, 3.5 g (21 mmol) of potassium iodide was added to the beaker and the contents were mixed to produce an aqueous composition. At the time of preparation, the potassium iodide was soluble in the aqueous composition. At 7 days after the preparation of the composition, the pH of the composition was 13.4.

At 38 days after the date of preparation of the aqueous composition, the composition included a crystalline precipitate, and 0.29 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 73

An aqueous composition was prepared as follows. A glass beaker was placed on a scale, and then, 36 g (99.5 mmol) of 25% sodium chlorite solution was placed in the beaker. Next, 2 ml of deionized water was added to the beaker. After adding the water, a magnetic stirrer was added to the beaker and the contents of the beaker were stirred. Next, 8 g (100 mmol) of the 50% sodium hydroxide solution was added to the beaker, and the contents of the beaker were further stirred. Next, 4 g (24 mmol) of potassium iodide was added to the beaker and the contents were mixed to produce an aqueous composition. At the time of preparation, the potassium iodide was soluble in the aqueous composition. At 7 days after the preparation of the composition, the pH of the composition was 13.5.

The aqueous composition was subject to an ion chromatography test, in order to determine the amounts of ions that were present in the composition 22 days after the date of preparation of the composition, using the same equipment described in sample 1. The results are shown in Table 2.

At 38 days after the date of preparation of the aqueous composition, the composition included a crystalline precipitate, and 0.25 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 74

An aqueous composition was prepared as follows. A glass beaker was placed on a scale, and then, 4.5 g (12.44 mmol) of 25% sodium chlorite solution was placed in the beaker. Next, 93 ml of deionized water was added to the beaker. After adding the water, a magnetic stirrer was added to the beaker and the contents of the beaker were stirred. Next, 0.57 g (2.1 mmol) of potassium peroxodisulfate (obtained from Merck, Germany) was added to the beaker and the contents of the beaker were further stirred. Next, 2 g (25 mmol) of the 50% sodium hydroxide solution was added to the beaker, and the contents were mixed to produce an aqueous composition. The composition appeared yellow at the time of preparation when the composition was prepared with sodium hydroxide and when sodium hydroxide was omitted from the composition. At the time of preparation of the composition including sodium hydroxide, the pH of the composition was 11.

A 1% acid use solution was prepared, as in sample 18; and on the date of preparation of the aqueous composition, an aliquot of the composition including sodium hydroxide was added to the 1% acid use solution, which did not appear to produce a reaction.

At 31 days after the date of preparation of the aqueous composition, the composition appeared clear, and 2 ml of the composition including sodium hydroxide was added to an acid use solution prepared in the same manner as in sample 1, in order to produce a chlorine dioxide test solution. The chlorine dioxide test solution was tested to measure absorbances, and the concentrations and yields were calculated

43 therefrom, as in sample 1. The absorbances, concentrations, and yields are listed in Table 3.

Sample 75

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 0.5 g (3 mmol) of potassium iodide and 1 g (12 mmol) of sodium acetate (obtained from VWR) were added to the beaker and the contents were mixed to produce an aqueous composition. The composition appeared clear at the time of preparation. At the time of preparation of the composition, the pH of the composition was 11.4.

A 1% acid use solution was prepared, as in sample 18; and on the date of preparation of the aqueous composition, an aliquot of the composition was added to the 1% acid use solution, which instantly produced a yellow colored solution and characteristic smell of chlorine dioxide.

The aqueous composition was subject to an ion chromatography test, in order to determine the amounts of ions that were present in the composition 15 days after the date of preparation of the composition, using the same equipment described in sample 1. The results are shown in Table 2.

Another aqueous composition was prepared in the same manner as sample 75, except that the potassium iodide was omitted; and an aliquot of the composition omitting potassium iodide was added to the 1% acid use solution prepared as in sample 18, which did not appear to produce a reaction.

At 31 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 76

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 3 g (17 mmol) of D-glucose (obtained from Merck, Germany) was added to the beaker and the contents were mixed to produce an aqueous composition. The composition appeared clear at the time of preparation. At the time of preparation of the composition, the pH of the composition was 10.9.

A 1% acid use solution was prepared, as in sample 18; and on the date of preparation of the aqueous composition, an aliquot of the composition was added to the 1% acid use solution, which produced a solution including yellow color and characteristic smell of chlorine dioxide after 10 minutes.

Within 1 month from the date of preparation of the aqueous composition, the composition reacted to form a solution including yellow coloration and characteristic smell of chlorine dioxide.

Sample 76'

An aqueous composition was prepared as follows. A glass beaker was placed on a scale, and then, 4.5 g (12.44 mmol) of 25% sodium chlorite solution was placed in the beaker. Next, 92.5 ml of deionized water was added to the beaker. After adding the water, a magnetic stirrer was added to the beaker and the contents of the beaker were stirred. Next, 3 g (17 mmol) of D-glucose was added to the beaker and the contents were mixed to produce an aqueous composition. The composition appeared clear at the time of preparation.

At 6 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 77

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 5 g (28 mmol) of D-glucose was added to the beaker and the contents were mixed to produce an aqueous composition.

Within 1 month from the date of preparation of the aqueous composition, the composition reacted to form a solution including yellow coloration and characteristic smell of chlorine dioxide.

Sample 77'

An aqueous composition was prepared as follows. A glass beaker was placed on a scale, and then, 4.5 g (12.44 mmol) of 25% sodium chlorite solution was placed in the beaker. Next, 90.5 ml of deionized water was added to the beaker. After adding the water, a magnetic stirrer was added to the beaker and the contents of the beaker were stirred. Next, 5 g (28 mmol) of D-glucose was added to the beaker and the contents were mixed to produce an aqueous composition. The composition appeared clear at the time of preparation.

At 6 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 78

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 0.5 g (2.8 mmol) of D-glucose was added to the beaker and the contents were mixed to produce an aqueous composition.

At 31 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 79

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 0.5 g (3.5 mmol) of anhydrous sodium sulfate was added to the beaker and the contents were mixed to produce an aqueous composition.

At 31 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 80

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 2 g (13 mmol) of sodium percarbonate and 0.5 g (4.9 mmol) of sodium bromide were added to the beaker and the contents were mixed to produce an aqueous composition.

At 31 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 81

An aqueous composition was prepared as follows. A glass beaker was placed on a scale, and then, 4.5 g (12.44 mmol) of 25% sodium chlorite solution was placed in the beaker. Next, 94.5 ml of deionized water was added to the beaker. After adding the water, a magnetic stirrer was added to the beaker and the contents of the beaker were stirred. Next, 0.5 g (5.1 mmol) of amidosulfonic acid was added to the beaker and the contents were mixed to produce an aqueous composition.

Sample 82

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.5 g (3 mmol) of potassium iodide and 2 g of Armohib 28(TM) were added to the beaker and the contents were mixed to produce an aqueous composition. The composition appeared brown with slight turbidity at the time of preparation. At the time of preparation of the composition, the pH of the composition was approximately 13 when tested with a pH test strip.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared brown, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 83

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 2 g (25 mmol) of the 50% sodium hydroxide solution was added to the beaker, and the contents of the beaker were further stirred. Next, 0.5 g (3 mmol) of potassium iodide and 2 g (6.7 mmol) of ATMP were added to the beaker and the contents were mixed to produce an aqueous composition. The composition appeared clear at the time of preparation. At the time of preparation of the composition, the pH of the composition was approximately 12 when tested with a pH test strip.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 84

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 2 g (25 mmol) of the 50% sodium hydroxide solution was added to the beaker, and the contents of the beaker were further stirred. Next, 0.5 g (3 mmol) of potassium iodide and 2 g (9.7 mmol) of HEDP were added to the beaker and the contents were mixed to produce an aqueous composition. The composition appeared clear at the time of preparation. At the time of preparation of the composition, the pH of the composition was approximately 13 when tested with a pH test strip.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 85

An aqueous composition was prepared as follows. A glass beaker was placed on a scale, and then, 4.5 g (12.44 mmol) of 25% sodium chlorite solution was placed in the beaker. Next, 92 ml of deionized water was added to the beaker. After adding the water, a magnetic stirrer was added to the beaker and the contents of the beaker were stirred. Next, 2 g (25 mmol) of the 50% sodium hydroxide solution was added to the beaker, and the contents of the beaker were further stirred. Next, 0.5 g (3 mmol) of potassium iodide and 2 g (7.4 mmol) of PBTC were added to the beaker and the contents were mixed to produce an aqueous composition. The composition appeared clear at the time of preparation. At the time of preparation of the composition, the pH of the composition was approximately 13 when tested with a pH test strip.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 86

An aqueous composition was prepared as follows. A glass beaker was placed on a scale, and then, 4.5 g (12.44 mmol) of 25% sodium chlorite solution was placed in the beaker. Next, 94.45 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.05 g (0.3 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 87

An aqueous composition was prepared as follows. A glass beaker was placed on a scale, and then, 4.5 g (12.44 mmol) of 25% sodium chlorite solution was placed in the beaker. Next, 94.4 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.1 g (0.6 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 88

An aqueous composition was prepared as follows. A glass beaker was placed on a scale, and then, 4.5 g (12.44 mmol) of 25% sodium chlorite solution was placed in the beaker. Next, 94.3 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.2 g (1.2 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 89

An aqueous composition was prepared as follows. A glass beaker was placed on a scale, and then, 4.5 g (12.44 mmol) of 25% sodium chlorite solution was placed in the beaker. Next, 94.2 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.3 g (1.8 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 90

An aqueous composition was prepared as follows. A glass beaker was placed on a scale, and then, 4.5 g (12.44 mmol) of 25% sodium chlorite solution was placed in the beaker. Next, 94.1 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.4 g (2.4 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 91

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.5 g (3 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 92

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 1 g (6 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 93

An aqueous composition was prepared as follows. A glass beaker was placed on a scale, and then, 4.5 g (12.44 mmol) of 25% sodium chlorite solution was placed in the beaker. Next, 92.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 2 g (12 mmol) of potassium iodide was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution which produced a solution including brown coloration a slight characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 94

An aqueous composition was prepared as follows. A glass beaker was placed on a scale, and then, 4.5 g (12.44 mmol) of 25% sodium chlorite solution was placed in the beaker. Next, 94.35 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.15 g (0.6 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 95

An aqueous composition was prepared as follows. A glass beaker was placed on a scale, and then, 4.5 g (12.44 mmol) of 25% sodium chlorite solution was placed in the beaker. Next, 94.2 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.3 g (1.2 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 96

An aqueous composition was prepared as follows. A glass beaker was placed on a scale, and then, 4.5 g (12.44 mmol) of 25% sodium chlorite solution was placed in the beaker. Next, 94.05 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.45 g (1.8 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 97

An aqueous composition was prepared as follows. A glass beaker was placed on a scale, and then, 4.5 g (12.44 mmol) of 25% sodium chlorite solution was placed in the beaker. Next, 93.9 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.6 g (2.4 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 98

An aqueous composition was prepared as follows. A glass beaker was placed on a scale, and then, 4.5 g (12.44 mmol) of 25% sodium chlorite solution was placed in the beaker. Next, 93.3 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 1.2 g (4.8 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 99

An aqueous composition was prepared as follows. A glass beaker was placed on a scale, and then, 4.5 g (12.44 mmol) of 25% sodium chlorite solution was placed in the beaker. Next, 91.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 3 g (12 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a rotten smell.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 100

An aqueous composition was prepared as follows. A glass beaker was placed on a scale, and then, 4.5 g (12.44 mmol) of 25% sodium chlorite solution was placed in the beaker. Next, 88.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 6 g (24 mmol) of sodium thiosulfate pentahydrate was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a rotten smell.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 101

An aqueous composition was prepared as follows. A glass beaker was placed on a scale, and then, 27 g (75 mmol) of 25% sodium chlorite solution was placed in the beaker. Next, 63.4 ml of deionized water was added to the beaker. After adding the water, a magnetic stirrer was added to the beaker and the contents of the beaker were stirred. Next, 6 g (75 mmol) of the 50% sodium hydroxide solution was added to the beaker, and the contents of the beaker were further stirred. Next, 3.6 g (14.5 mmol) of sodium thiosulfate pentahydrate was added to the beaker and the contents were mixed to produce an aqueous composition. At the time of preparation, the composition appeared slightly yellow, which was apparently caused by the high concentration of sodium chlorite A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 3 days after the date of preparation of the aqueous composition, the composition appeared clear, and 0.33 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 102

An aqueous composition was prepared as follows. A glass beaker was placed on a scale, and then, 4.5 g (12.44 mmol) of 25% sodium chlorite solution was placed in the beaker. Next, 94.3 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.2 g (1.6 mmol) of sodium sulfite was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 2 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 103

An aqueous composition was prepared as follows. A glass beaker was placed on a scale, and then, 4.5 g (12.44 mmol) of 25% sodium chlorite solution was placed in the beaker. Next, 94.11 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.39 g (3.1 mmol) of sodium sulfite was added to the beaker and the contents were mixed to produce an aqueous composition. The composition appeared clear at the time of preparation.

A 1% acid use solution was prepared, as in sample 18; and at on the date of preparation of the aqueous composition, an aliquot of the composition was added to the 1% acid use solution, which produced a solution including yellow coloration and characteristic smell of chlorine dioxide.

At 2 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 104

An aqueous composition was prepared as follows. A glass beaker was placed on a scale, and then, 4.5 g (12.44 mmol) of 25% sodium chlorite solution was placed in the beaker. Next, 93.72 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.78 g (6.2 mmol) of sodium sulfite was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 2 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 105

An aqueous composition was prepared as follows. A glass beaker was placed on a scale, and then, 4.5 g (12.44 mmol) of 25% sodium chlorite solution was placed in the beaker. Next, 92.94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 1.56 g (12.4 mmol) of sodium sulfite was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 2 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 106

An aqueous composition was prepared as follows. A glass beaker was placed on a scale, and then, 4.5 g (12.44 mmol) of 25% sodium chlorite solution was placed in the beaker. Next, 94.25 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.25 g (4.1 mmol) of monoethanolamine was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 5 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 107

An aqueous composition was prepared as follows. A glass beaker was placed on a scale, and then, 4.5 g (12.44 mmol) of 25% sodium chlorite solution was placed in the beaker.

Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.5 g (8.2 mmol) of monoethanolamine was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 5 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 108

An aqueous composition was prepared as follows. A glass beaker was placed on a scale, and then, 4.5 g (12.44 mmol) of 25% sodium chlorite solution was placed in the beaker. Next, 93.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 1 g (16.4 mmol) of monoethanolamine was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 5 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 109

An aqueous composition was prepared as follows. A glass beaker was placed on a scale, and then, 4.5 g (12.44 mmol) of 25% sodium chlorite solution was placed in the beaker. Next, 92.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 2 g (32.7 mmol) of monoethanolamine was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 5 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 110

An aqueous composition was prepared as follows. A glass beaker was placed on a scale, and then, 4.5 g (12.44 mmol) of 25% sodium chlorite solution was placed in the beaker. Next, 90.5 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 4 g (65.5 mmol) of monoethanolamine was added to the beaker and the contents were mixed to produce an aqueous composition. The composition appeared clear at the time of preparation.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

At 5 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 111

An aqueous composition was prepared as follows. A glass beaker was placed on a scale, and then, 4.5 g (12.44 mmol) of 25% sodium chlorite solution was placed in the beaker. Next, 93.87 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.63 g (5.0 mmol) of sodium sulfite was added to the beaker and the contents were mixed to produce an aqueous composition.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 112

An aqueous composition was prepared as follows. A glass beaker was placed on a scale, and then, 4.5 g (12.44 mmol) of 25% sodium chlorite solution was placed in the beaker. Next, 94.19 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.31 g (2.5 mmol) of sodium sulfite was added to the beaker and the contents were mixed to produce an aqueous composition.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 113

An aqueous composition was prepared as follows. A glass beaker was placed on a scale, and then, 4.5 g (12.44 mmol) of 25% sodium chlorite solution was placed in the beaker. Next, 94.29 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.21 g (1.7 mmol) of sodium sulfite was added to the beaker and the contents were mixed to produce an aqueous composition.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 114

An aqueous composition was prepared as follows. A glass beaker was placed on a scale, and then, 4.5 g (12.44 mmol) of 25% sodium chlorite solution was placed in the beaker. Next, 94.34 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.16 g (1.3 mmol) of sodium sulfite was added to the beaker and the contents were mixed to produce an aqueous composition.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 115

An aqueous composition was prepared as follows. A glass beaker was placed on a scale, and then, 4.5 g (12.44 mmol) of 25% sodium chlorite solution was placed in the beaker. Next, 94.3 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.27 g (0.63 mmol) of sodium sulfite was added to the beaker and the contents were mixed to produce an aqueous composition.

At 4 days after the date of preparation of the aqueous composition, the composition appeared clear, and 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 116

An aqueous composition was prepared as follows. A glass beaker was placed on a scale, and then, 4.5 g (12.44 mmol) of 25% sodium chlorite solution was placed in the beaker. Next, 94.3 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.27 g (1.7 mmol) of anhydrous zinc sulfate (obtained from VWR) was added to the beaker and the contents were mixed to produce an aqueous composition. The composition included white crystals at the time of preparation. After the preparation of the composition, the pH of the composition was 12.8.

A 1% acid use solution was prepared, as in sample 18; and 1 day after the date of preparation of the aqueous composition, an aliquot of the composition was added to the 1% acid use solution, which did not appear to produce a reaction.

On the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 117

An aqueous composition was prepared as follows. A glass beaker was placed on a scale, and then, 4.5 g (12.44 mmol) of 25% sodium chlorite solution was placed in the beaker. Next, 94.11 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.8 g (1.7 mmol) of ammonium iron (III) sulfate dodecahydrate (obtained from Merck) was added to the beaker and the contents were mixed to produce an aqueous composition. The composition included brown crystals at the time of preparation. After the preparation of the composition, the pH of the composition was 12.3.

A 1% acid use solution was prepared, as in sample 18; and at 1 day after the date of preparation of the aqueous composition, an aliquot of the composition was added to the 1% acid use solution, which produced a solution having with a light yellow color and characteristic smell of chlorine dioxide.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 118

An aqueous composition was prepared as follows. A glass beaker was placed on a scale, and then, 4.5 g (12.44 mmol) of 25% sodium chlorite solution was placed in the beaker. Next, 93.72 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.28 g (1.6 mmol) of silver nitrate (obtained from Merck) was added to the beaker and the contents were mixed to produce an aqueous composition. The composition included grey crystals at the time of preparation. After the preparation of the composition, the pH of the composition was 12.7.

A 1% acid use solution was prepared, as in sample 18; and at 1 day after the date of preparation of the aqueous composition, an aliquot of the composition was added to the 1% acid use solution, which did not appear to produce a reaction.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 119

An aqueous composition was prepared as follows. A glass beaker was placed on a scale, and then, 4.5 g (12.44 mmol) of 25% sodium chlorite solution was placed in the beaker. Next, 92.94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.17 g (1.7 mmol) of potassium nitrate (obtained from Merck) was added to the beaker and the contents were mixed to produce an aqueous composition. The composition appeared clear at the time of preparation. After the preparation of the composition, the pH of the composition was 12.7.

A 1% acid use solution was prepared, as in sample 18; and at 1 day after the date of preparation of the aqueous composition, an aliquot of the composition was added to the 1% acid use solution, which did not appear to produce a reaction.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 120

An aqueous composition was prepared as follows. A glass beaker was placed on a scale, and then, 4.5 g (12.44 mmol) of 25% sodium chlorite solution was placed in the beaker. Next, 94.25 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.48 g (1.6 mmol) of cobalt(II) nitrate hexahydrate (obtained from Merck) was added to the beaker and the contents were mixed to produce an aqueous composition. The composition included black crystals at the time of preparation. After the preparation of the composition, the pH of the composition was 12.5.

A 1% acid use solution was prepared, as in sample 18; and at 1 day after the date of preparation of the aqueous composition, an aliquot of the composition was added to the 1% acid use solution, which did not appear to produce a reaction.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 121

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.27 g (1.7 mmol) of iron(III) oxide (obtained from Merck) was added to the beaker and the contents were mixed to produce an aqueous composition. The composition included red crystals at the time of preparation. After the preparation of the composition, the pH of the composition was 12.8.

A 1% acid use solution was prepared, as in sample 18; and at 1 day after the date of preparation of the aqueous composition, an aliquot of the composition was added to the 1% acid use solution, which did not appear to produce a reaction.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 122

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.45 g (1.7 mmol) of iron(III) chloride hexahydrate (obtained from Merck) was added to the beaker and the contents were mixed to produce an aqueous composition. The composition included brown crystals at the time of preparation. After the preparation of the composition, the pH of the composition was 12.4.

A 1% acid use solution was prepared, as in sample 18; and at 1 days after the date of preparation of the aqueous composition, an aliquot of the composition was added to the 1% acid use solution, which produced a solution including yellow coloration and characteristic smell of chlorine dioxide.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 123

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.33 g (1.7 mmol) of iron(II) chloride tetrahydrate (obtained from Merck) was added to the beaker and the contents were mixed to produce an aqueous composition. The composition included brown crystals at the time of preparation. After the preparation of the composition, the pH of the composition was 12.5.

A 1% acid use solution was prepared, as in sample 18; and at 1 day after the date of preparation of the aqueous composition, an aliquot of the composition was added to the 1% acid use solution, which produced a solution including some yellow coloration and characteristic smell of chlorine dioxide.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 124

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.32 g (1.7 mmol) of anhydrous tin(II) chloride (obtained from Alfa Aesar, Germany) was added to the beaker and the contents were mixed to produce an aqueous composition. The composition appeared clear at the time of preparation. After the preparation of the composition, the pH of the composition was 12.3.

A 1% acid use solution was prepared, as in sample 18; and at 1 day after the date of preparation of the aqueous composition, an aliquot of the composition was added to the 1% acid use solution, which did not appear to produce a reaction.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 125

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.13 g (1.7 mmol) of thiourea (obtained from Merck) was added to the beaker and the contents were mixed to produce an aqueous composition. The composition appeared clear at the time of preparation. After the preparation of the composition, the pH of the composition was 12.7.

A 1% acid use solution was prepared, as in sample 18; and at 1 day after the date of preparation of the aqueous composition, an aliquot of the composition was added to the 1% acid use solution, which produced a solution including yellow coloration and characteristic smell of chlorine dioxide.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 126

An aqueous composition was prepared as follows. A glass beaker was placed on a scale, and then, 4.5 g (12.44 mmol)

of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.58 g (1.7 mmol) of sodium dithionite (50%; Blankit obtained from BASF) was added to the beaker and the contents were mixed to produce an aqueous composition. The composition appeared light yellow at the time of preparation. After the preparation of the composition, the pH of the composition was 12.7.

A 1% acid use solution was prepared, as in sample 18; and at 1 day after the date of preparation of the aqueous composition, an aliquot of the composition was added to the 1% acid use solution, which produced a solution including yellow coloration and characteristic smell of chlorine dioxide.

At 1 day after the date of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 127

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.1 g (1.7 mmol) of urea was added to the beaker and the contents were mixed to produce an aqueous composition. The composition appeared clear at the time of preparation. On the date of preparation of the composition, the pH of the composition was 12.9.

A 1% acid use solution was prepared, as in sample 18; and on the date of preparation of the aqueous composition, an aliquot of the composition was added to the 1% acid use solution, which did not appear to produce a reaction.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 128

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.52 g (3.3 mmol) of sodium percarbonate was added to the beaker and the contents were mixed to produce an aqueous composition. The composition appeared clear at the time of preparation. On the date of preparation of the composition, the pH of the composition was 12.7.

A 1% acid use solution was prepared, as in sample 18; and on the date of preparation of the aqueous composition, an aliquot of the composition was added to the 1% acid use solution, which produced a solution including yellow coloration and characteristic smell of chlorine dioxide.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 129

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.25 g (1.3 mmol) of sodium disulfite was added to the beaker and the contents were mixed to produce an aqueous composition. The composition appeared clear at the time of preparation. On the date of preparation of the composition, the pH of the composition was 12.8.

A 1% acid use solution was prepared, as in sample 18; and on the date of preparation of the aqueous composition, an aliquot of the composition was added to the 1% acid use solution, which did not appear to produce a reaction.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 130

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.25 g (1.7 mmol) of triethanolamine was added to the beaker and the contents were mixed to produce an aqueous composition. The composition appeared clear at the time of preparation. On the date of preparation of the composition, the pH of the composition was 12.9.

A 1% acid use solution was prepared, as in sample 18; and on the date of preparation of the aqueous composition, an aliquot of the composition was added to the 1% acid use solution, which produced a solution including some yellow coloration and characteristic smell of chlorine dioxide.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 131

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.48 g of Trilon® BX liquid containing 40% ethylenediaminetetraacetic acid (EDTA) was added to the beaker and the contents were mixed to produce an aqueous composition. The composition appeared clear at the time of preparation. On the date of preparation of the composition, the pH of the composition was 12.9.

A 1% acid use solution was prepared, as in sample 18; and on the date of preparation of the aqueous composition, an aliquot of the composition was added to the 1% acid use solution, which did not appear to produce a reaction.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 132

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.1 g (1.6 mmol) of boric acid was added to the beaker and the contents were mixed to produce an aqueous composition. The composition appeared clear at the time of preparation. On the date of preparation of the composition, the pH of the composition was 12.9.

A 1% acid use solution was prepared, as in sample 18; and on the date of preparation of the aqueous composition, an aliquot of the composition was added to the 1% acid use solution, which did not appear to produce a reaction.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 133

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.08 g (1.5 mmol) of 85% formic acid was added to the beaker and the contents were mixed to produce an aqueous composition. The composition appeared clear at the time of preparation. On the date of preparation of the composition, the pH of the composition was 12.9.

A 1% acid use solution was prepared, as in sample 18; and on date of preparation of the aqueous composition, an aliquot of the composition was added to the 1% acid use solution, which produced a solution including yellow coloration and characteristic smell of chlorine dioxide.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

Sample 134

An aqueous composition was prepared as follows. A glass beaker was placed on a scale, and then, 4.5 g (12.44 mmol) of 25% sodium chlorite solution was placed in the beaker. Next, 94 ml of deionized water was added to the beaker. After adding the water, a magnetic stirrer was added to the beaker and the contents of the beaker were stirred. Next, 1 g (12.5 mmol) of the 50% sodium hydroxide solution was added to the beaker, and the contents of the beaker were further stirred. Next, 0.23 g (1.7 mmol) of zinc chloride was added to the beaker and the contents were mixed to produce an aqueous composition. The composition included white crystals at the time of preparation. On the date of preparation of the composition, the pH of the composition was 12.8.

A 1% acid use solution was prepared, as in sample 18; and on the date of preparation of the aqueous composition, an aliquot of the composition was added to the 1% acid use solution, which did not appear to produce a reaction.

On the day of preparation of the aqueous composition, 2 ml of the composition was added to an acid use solution prepared in the same manner as in sample 1, in order to produce a chlorine dioxide test solution. The chlorine dioxide test solution was tested to measure absorbances, and the concentrations and yields were calculated therefrom, as in sample 1. The absorbances, concentrations, and yields are listed in Table 3.

The ion chromatography results of the samples above show, at least, the stability of the iodide in select samples of aqueous composition, the stability of thiosulfate in select samples of aqueous composition, and stability of the chlorite ions in select samples of aqueous composition. For example, the ion chromatography results show the decreased oxidation of iodide to iodate in select samples of aqueous composition.

FIG. 1 illustrates a graph of yield of chlorine dioxide versus molar ratio of sodium chlorite to activator. The percent yields of chlorine dioxide after 1 minute of contact time between the acid use solution and aqueous compositions of samples 86 through 115 (see Table 3) were plotted against the molar ratio of sodium chlorite to the respective activator (see Table 1). Samples 86 through 115 included potassium iodide, sodium thiosulfate, sodium sulfite, or methanolamine (MEA). It was found that when potassium iodide is included in an aqueous composition at molar ratios of from 40:1 to 1:1 of sodium chlorite to potassium iodide, the aqueous composition provided superior yield when contacted with an acid. It was also found that when sodium thiosulfate is included in an aqueous composition at molar ratios of from 20:1 to 2:1 of sodium chlorite to sodium thiosulfate, the aqueous composition provided superior yield when contacted with an acid.

TABLE 1

Sample No.

| | 1 | 2 | 3 | 4 | 5 | 6 | 7 | 7' | 8 | 9 | 10 | 11 | 12 | 12' | 13 | 14 | 15 | 16 | 17 | 18 | 19 | 20 | 21 | 22 | 23 |
|---|---|---|---|---|---|---|---|---|---|---|---|---|---|---|---|---|---|---|---|---|---|---|---|---|---|
| NaClO$_2$ (25% solution) (g) | 4.5 | 90 | 4.5 | | | | 9 | 9 | 9 | 9 | 9 | 9 | 9 | 9 | 9 | 9 | 9 | 9 | 9 | 4.5 | 4.5 | 4.5 | 4.5 | 4.5 | 4.5 |
| KI (g) | 0.5 | 10 | | 90 | 0.5 | 10 | 1 | 1 | 1 | 1 | 1 | 1 | 1 | 1 | 1 | 1 | 1 | 1 | 1 | 0.5 | 0.5 | 0.5 | 0.5 | 1.5 | 1.5 |
| Deionized H$_2$O (ml) | 95 | | 95.5 | 10 | 99.5 | 90 | 90 | 90 | 90 | 90 | 90 | 90 | 90 | 90 | 90 | 90 | 90 | 90 | 90 | 95 | 94 | 92 | 90 | 94 | 91 |
| NaOH (50% solution) (g) | | | | | | | | | | | | | | 2 | | 1.2 | 0.6 | 0.6 | 0.5 | | | 3 | 5 | | 3 |
| ATMP (g) | | | | | | | | | 1 | | | | 2 | | | | | 1 | 1 | | 1 | | | | |
| Ascorbic Acid (g) | | | | | | | | | | 1 | | | | | | | | | | | | | | | |
| Acetic Acid (60% solution) (g) | | | | | | | | | | | 0.1 | | | | | | | | | | | | | | |
| Boric Acid (g) | | | | | | | | | | | | 0.04 | | | | | | | | | | | | | |
| Sorbic Acid (g) | | | | | | | | | | | | 0.04 | | | | | | | | | | | | | |
| Citric Acid monohydrate (g) | | | | | | | | | | | | | | | | 1 | | | | | | | | | |
| NaI (g) | | | | | | | | | | | | | | | 1 | | | | | | | | | | |

Sample No.

| | 24 | 25 | 26 | 27 | 28 | 29 | 30 | 31 | 32 | 33 | 34 | 35 | 36 | 37 | 38 | 39 | 40 | 41 | 41' | 42 | 43 | 44 | 45 |
|---|---|---|---|---|---|---|---|---|---|---|---|---|---|---|---|---|---|---|---|---|---|---|---|
| NaClO$_2$ (25% solution) (g) | 9 | 18 | 9 | 9 | 18 | 27 | 36 | 4.5 | 4.5 | 9.5 | 4.5 | 4.5 | 4.5 | 4.5 | 4.5 | 4.5 | 4.5 | 4.5 | 4.5 | 4.5 | 4.5 | 4.5 | 4.5 |
| KI (g) | 1 | 2 | 3 | 1 | 2 | 3 | 4 | 1 | | | 0.15 | | | 0.5 | 0.5 | | | | | | | | |
| Deionized H$_2$O (ml) | 90 | 80 | 88 | 85 | 75 | 55 | 40 | 94 | 92 | 88 | 94.75 | 92 | 92 | 93 | 93 | 93.5 | 93.5 | 93.5 | 94.5 | 93.5 | 93.5 | 93.5 | 93.5 |
| NaOH (50% solution) (g) | | | | 5 | 5 | 15 | 20 | | | | | | 1 | | | | | | | | | | |
| NaBr (g) | | | | | | | | 0.5 | 0.95 | 0.9 | 0.25 | 1 | | | | | | | | | | | |
| Iodine (g) | | | | | | | | | 1.5 | 2.5 | | 5 | | | | | | | | | | | |
| Sodium Thiosulfate (g) | | | | | | | | | | | 0.35 | | | | | | | | | | | | |
| Na$_2$CO$_3$ (g) | | | | | | | | | | | | | 0.6 | | | | | | | | | | |
| Sodium Silicate (g) | | | | | | | | | | | | | | 2 | | | | | | | | | |
| KMnO$_4$ (g) | | | | | | | | | | | | | | | 2 | | | | | | | | |
| Amino Thiocyanate (g) | | | | | | | | | | | | | | | | 0.8 | | | | | | | |
| Urea (g) | | | | | | | | | | | | | | | | | 1 | | | | | | |
| Sodium Percarbonate (g) | | | | | | | | | | | | | | | | | | 1 | 1 | | | | |
| Sodium Peroxodisulfate (g) | | | | | | | | | | | | | | | | | | | | 1 | | | |
| Sodium Sulfite (g) | | | | | | | | | | | | | | | | | | | | | 1 | | |
| Sodium Disulfite (g) | | | | | | | | | | | | | | | | | | | | | | 1 | |
| | | | | | | | | | | | | | | | | | | | | | | | 1 |

Sample No.

| | 46 | 47 | 48 | 48' | 49 | 50 | 51 | 51' | 52 | 53 | 54 | 55 | 56 | 57 | 58 | 59 | 60 | 61 | 62 |
|---|---|---|---|---|---|---|---|---|---|---|---|---|---|---|---|---|---|---|---|
| NaClO$_2$ (25% solution) (g) | 4.5 | 4.5 | 9 | 9 | 9 | 4.5 | 4.5 | 4.5 | 4.5 | 4.5 | 4.5 | 4.5 | 4.5 | 4.5 | 4.5 | 4.5 | 4.5 | 4.5 | 4.5 |
| KI (g) | | 0.1 | | | | 0.5 | | | | | | | | | | | | | |
| Deionized H$_2$O (ml) | 93.5 | 93.9 | 89 | 89 | 89 | 93 | 95.2 | 95.2 | 94.5 | 92.5 | 93.5 | 94.5 | 93.5 | 93.5 | 93.5 | 93.5 | 94.2 | 93 | 93.5 |
| NaOH (50% solution) (g) | | 1 | | | | | | | | | | | | | | | 1 | | |
| NaBr (g) | | 0.5 | | | | | 0.3 | 0.3 | 0.3 | | | | | | | | | | |
| Sodium Thiosulfate (g) | | | | | | | | | | | | | | | | | | | |
| Na$_2$CO$_3$ (g) | | | | | | | | | 1 | 3 | | 1 | | | | | | | |
| Urea (g) | | | | | | | | | | | 2 | | 2 | | | | | | |
| Sodium Percarbonate (g) | | | | | | | | | | | | | | 1 | | | | | |
| Sodium Peroxodisulfate (g) | | | | | | | | | | | | | | | 1 | | | | |
| | | | | | | | | | | | | | | | | 1 | | | |
| | | | | | | | | | | | | | | | | | | 0.28 | 0.56 |
| | | | | | | | | | | | | | | | | | | | 1 |

TABLE 1-continued

| | Sample No. | | | | | | | | | | | | | | | | | | | | |
|---|---|---|---|---|---|---|---|---|---|---|---|---|---|---|---|---|---|---|---|---|---|
| | 63 | 64 | 65 | 66 | 67 | 68 | 69 | 70 | 71 | 72 | 73 | 74 | 75 | 76 | 77 | 77' | 78 | 79 | 80 | 81 | 82 |
| Sodium Sulfite (g) | | | | | | | | | | | | | | | | | | | | | |
| Monoethanolamine (g) | | | 2 | | | | | | | | | | | | | | | | 2 | | |
| Triethanolamine (g) | | 2 | | 2 | | 2 | | | | | | | | 2 | | | 2 | | | | |
| Rewocid WK 30 (g) | | | | | 2 | | | | | | | | 2 | | | | | | | | |
| Trilon BX (40% EDTA) (g) | | | | | | | | | | | 2 | | | | 2 | | | 2 | | | |
| Trilon M (40% MGDA) (g) | | | | | | | | | | | | 2 | | | | | | | | | |
| Potassium Thiocyanate (g) | 1 | | | | | | | | | | | | | | | | | | | | |
| Sodium Sulfate (g) | | | | | | | | | | | | | | | | | | | | | 2 |
| NaClO$_2$ (25% solution) (g) | 4.5 | 4.5 | 2 | 4 | 9 | 9 | 36 | 22.5 | 27 | 31.5 | 36 | 4.5 | 4.5 | 4.5 | 4.5 | 4.5 | 4.5 | 4.5 | 4.5 | 4.5 | 4.5 |
| KI (g) | 0.5 | 0.5 | 0.5 | 0.4 | 1 | 1 | 4 | 2.5 | 3 | 3.5 | 4 | | 0.5 | | | | | | | | 0.5 |
| Deionized H$_2$O (ml) | 91.5 | 90 | 97.7 | 95.5 | 89 | 89 | | 20 | 14 | 8 | 2 | 93 | 94 | 92.5 | 94.5 | 90.5 | 94.5 | 94.5 | 94.5 | 94.5 | 92 |
| NaOH (50% solution) (g) | | 5 | 2 | 1 | | | 10 | 5 | 6 | 7 | 8 | 2 | 1 | | | | | | | | 1 |
| Sodium Percarbonate (g) | 4 | | | | | | | | | | | | | | | | | | | | |
| Sodium Sulfite (g) | | | | | | | | | | | | | | | | | | | 2 | | |
| Calcium Ascorbate (g) | | | | | | | | | | | | | | | | | | 0.5 | | | |
| Borate (g) | | | | | | 1 | | | | | | | | | | | | | | | |
| Potassium Peroxodisulfate (g) | | | | | | | | | | | | 0.57 | | | | | | | | | |
| Sodium Acetate (g) | | | | | | | | | | | | | 1 | | | | | | | | |
| D-Glucose (g) | | | | | | | | | | | | | | 3 | 5 | 5 | 0.5 | | | | |
| NaBr (g) | | | | | | | | | | | | | | | | | | | | 0.5 | |
| Amidosulfonic Acid (g) | | | | | | | | | | | | | | 3 | | | | | | | |
| Armohib 28 (g) | | | | | | | | | | | | | | | | | | | | | 2 |

| | Sample No. | | | | | | | | | | | | | | | | | | |
|---|---|---|---|---|---|---|---|---|---|---|---|---|---|---|---|---|---|---|---|
| | 83 | 84 | 85 | 86 | 87 | 88 | 89 | 90 | 91 | 92 | 93 | 94 | 95 | 96 | 97 | 98 | 99 | 100 | 101 |
| NaClO$_2$ (25% solution) (g) | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 27 |
| KI (g) | 0.5 | 0.5 | 0.5 | 0.05 | 0.1 | 0.2 | 0.3 | 0.4 | 0.5 | 1 | 2 | 1 | 1 | 1 | 1 | 1 | 1 | 1 | 63.4 |
| Deionized H$_2$O (ml) | 92 | 92 | 92 | 94.45 | 94.4 | 94.3 | 94.25 | 94.1 | 94 | 93.5 | 92.5 | 94.35 | 94.2 | 94.05 | 93.9 | 93.3 | 91.5 | 88.5 | |
| NaOH (50% solution) (g) | 2 | 2 | 2 | 1 | 1 | 1 | 1 | 1 | 1 | 1 | 1 | 1 | 1 | 1 | 1 | 1 | 1 | 1 | 6 |
| Sodium Thiosulfate (g) | | | | | | | | | | | | 0.15 | 0.3 | 0.45 | 0.6 | 1.2 | 3 | 6 | 3.6 |
| ATMP (g) | 2 | | | | | | | | | | | | | | | | | | |
| HEDP (g) | | 2 | | | | | | | | | | | | | | | | | |
| PBTC (g) | | | 2 | | | | | | | | | | | | | | | | |
| Approximate Molar Ratio of NaClO$_2$ to Activator | | | | 40:1 | 20:1 | 10:1 | 7.5:1 | 5:1 | 4:1 | 2:1 | 1:1 | 20:1 | 10:1 | 7.5:1 | 5:1 | 2.5:1 | 1:1 | 1:2 | |

| | Sample No. | | | | | | | | | | | | | |
|---|---|---|---|---|---|---|---|---|---|---|---|---|---|---|
| | 102 | 103 | 104 | 105 | 106 | 107 | 108 | 109 | 110 | 111 | 112 | 113 | 114 | 115 |
| NaClO$_2$ (25% solution) (g) | 4.5 | 4.5 | 4.5 | 4.5 | 4.5 | 4.5 | 4.5 | 4.5 | 4.5 | 4.5 | 4.5 | 4.5 | 4.5 | 4.5 |
| Deionized H$_2$O (ml) | 94.3 | 94.11 | 93.72 | 92.94 | 94.25 | 94 | 93.5 | 92.5 | 90.5 | 93.87 | 94.19 | 94.29 | 94.34 | 94.42 |
| NaOH (50% solution) (g) | 1 | 1 | 1 | 1 | 1 | 1 | 1 | 1 | 1 | 1 | 1 | 1 | 1 | 1 |
| Sodium Sulfite (g) | 0.2 | 0.39 | 0.78 | 1.56 | | | | | | 0.63 | 0.31 | 0.21 | 0.16 | 0.08 |

TABLE 1-continued

| | Sample No. | | | | | | | | | | | | | | | | | | |
|---|---|---|---|---|---|---|---|---|---|---|---|---|---|---|---|---|---|---|---|
| | 116 | 117 | 118 | 119 | 120 | 121 | 122 | 123 | 124 | 125 | 126 | 127 | 128 | 129 | 130 | 131 | 132 | 133 | 134 |
| Monoethanolamine (g) | | | | | | | 0.25 | 0.5 | 1 | 2 | 4 | | | | | | | | |
| Approximate Molar Ratio of NaClO$_2$ to Activator | 8:1 | 4:1 | 4:1 | 2:1 | 1:1 | 1:1 | 4:1 | 2:1 | 1:1 | 1:2 | 1:4 | 1:4 | 2.5:1 | 5:1 | 7.5:1 | 10:1 | | 20:1 | |
| NaClO$_2$ (25% solution) (g) | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 | 4.5 |
| Deionized H$_2$O (ml) | 94.3 | 94.11 | 93.72 | 92.94 | 94.25 | 94 | 94 | 94 | 94 | 94 | 94 | 94 | 94 | 94 | 94 | 94 | 94 | 94 | 94 |
| NaOH (50% solution) (g) | 1 | 1 | 1 | 1 | 1 | 1 | 1 | 1 | 1 | 1 | 1 | 1 | 1 | 1 | 1 | 1 | 1 | 1 | 1 |
| Zinc Sulfate (g) | 0.27 | | | | | | | | | | | | | | | | | | |
| Ammonium Iron(III) Sulfate Dodecahydrate (g) | | 0.8 | | | | | | | | | | | | | | | | | |
| AgNO$_3$ (g) | | | 0.28 | | | | | | | | | | | | | | | | |
| KNO$_3$ (g) | | | | 0.17 | | | | | | | | | | | | | | | |
| Cobalt(II) Nitrate Hexahydrate (g) | | | | | 0.48 | | | | | | | | | | | | | | |
| Iron(III) Oxide (g) | | | | | | 0.27 | | | | | | | | | | | | | |
| Iron(III) Chloride Hexahydrate (g) | | | | | | | 0.45 | | | | | | | | | | | | |
| Iron(II) Chloride Tetrahydrate (g) | | | | | | | | 0.33 | | | | | | | | | | | |
| Anhydrous Tin(II) Chloride (g) | | | | | | | | | 0.32 | | | | | | | | | | |
| Thiourea (g) | | | | | | | | | | 0.13 | | | | | | | | | |
| Sodium Dithionite (50%) (g) | | | | | | | | | | | 0.58 | | | | | | | | |
| Urea (g) | | | | | | | | | | | | 0.1 | | | | | | | |
| Sodium Percarbonate (g) | | | | | | | | | | | | | 0.52 | | | | | | |
| Sodium Disulfite (g) | | | | | | | | | | | | | | 0.25 | | | | | |
| Triethanolamine (g) | | | | | | | | | | | | | | | 0.25 | | | | |
| Trilon BX (40% EDTA) (g) | | | | | | | | | | | | | | | | 0.48 | | | |
| Boric Acid (g) | | | | | | | | | | | | | | | | | 0.1 | | |
| Formic Acid (85%) (g) | | | | | | | | | | | | | | | | | | 0.08 | |
| Zinc Chloride (g) | | | | | | | | | | | | | | | | | | | 0.23 |

TABLE 2

| | Sample No. | | | | | | | | | | | |
|---|---|---|---|---|---|---|---|---|---|---|---|---|
| | 1 | 3 | 7 | 7' | 12 | 12 | 13 | 13 | 18 | 18 | 19 | 19 |
| Sample Age at Time of Test (days) | 220 | 220 | 56 | 126 | 174 | 56 | 126 | 126 | 31 | 101 | 31 | 101 |
| Calculated Original Concentration of Chlorite (ppm) | 11250 | 11250 | 22500 | 22500 | 22500 | 22500 | 22500 | 22500 | 11250 | 11250 | 11250 | 11250 |
| Calculated Original Concentration of Iodide (ppm) | 5000 | | 10000 | 10000 | 10000 | 10000 | 10000 | 10000 | 5000 | 5000 | 5000 | 5000 |
| Chloride Concentration at Time of Test (ppm) | 935 | 92 | 5028 | 4819 | 687 | 977 | 1633 | 5566 | 888 | 1635 | 144 | 261 |
| Chlorite Concentration at Time of Test (ppm) | 7637 | 9159 | 16786 | 15846 | 7284 | 22595 | 20034 | 15031 | 7543 | 5454 | 9156 | 8239 |
| Chlorite Remaining at Time of Test (%) | 68 | 81 | 75 | 70 | 32 | 100 | 89 | 67 | 67 | 48 | 81 | 73 |
| Chlorate Concentration at Time of Test (ppm) | 43 | 45 | 130 | 136 | 42 | 121 | 123 | 135 | 45 | 48 | 0 | 43 |
| Iodide Concentration at Time of Test (ppm) | 1851 | 0 | 0 | 0 | 2197 | 9879 | 7480 | 0 | 1902 | 0 | 4169 | 3492 |
| Iodide Remaining at Time of Test (%) | 37 | | 0 | 0 | 22 | 99 | 75 | 0 | 38 | 0 | 83 | 70 |
| Iodate Concentration at Time of Test (ppm) | 2782 | 0 | 16211 | 16208 | 1933 | 1887 | 4317 | 18584 | 2580 | 5398 | 140 | 517 |

| | Sample No. | | | | | | | | |
|---|---|---|---|---|---|---|---|---|---|
| | 20 | 21 | 24 | 25 | 27 | 28 | 34 | 35 | 36 |
| Sample Age at Time of Test (days) | 32 | 101 | 101 | 101 | 101 | 101 | 48 | 48 | 48 |
| Calculated Original Concentration of Chlorite (ppm) | 11250 | 11250 | 22500 | 45000 | 22500 | 45000 | 11250 | 11250 | 11250 |
| Calculated Original Concentration of Iodide (ppm) | 5000 | 5000 | 10000 | 20000 | 10000 | 20000 | 8500 | | |
| Calculated Original Concentration of Activator (ppm) | | | | | | | | 50000 | 3822 |
| Chloride Concentration at Time of Test (ppm) | 131 | 231 | 1294 | 3846 | 885 | 2866 | 241 | 119 | 411 |
| Chlorite Concentration at Time of Test (ppm) | 9189 | 8503 | 15214 | 29400 | 17002 | 32323 | 8359 | 9960 | 9177 |
| Chlorite Remaining at Time of Test (%) | 82 | 76 | 68 | 65 | 76 | 72 | 74 | 89 | 82 |
| Chlorate Concentration at Time of Test (ppm) | 0 | 46 | 93 | 188 | 98 | 197 | 45 | 0 | 58 |
| Iodide Concentration at Time of Test (ppm) | 1991 | 3817 | 5123 | 7775 | 6912 | 11152 | 3810 | 0 | |
| Iodide Remaining at Time of Test (%) | 40 | 76 | 51 | 39 | 69 | 56 | 45 | | |
| Iodate Concentration at Time of Test (ppm) | 124 | 436 | 3615 | 11779 | 2118 | 7919 | 1162 | 0 | |
| Bromide Concentration at Time of Test (ppm) | | | | | | | | 59659 | |
| Bromide Remaining at Time of Test (%) | | | | | | | | 119 | |
| Thiosulfate Concentration at Time of Test (ppm) | | | | | | | | | 733 |
| Thiosulfate Remaining at Time of Test (%) | | | | | | | | | 19 |
| Sulfate Concentration at Time of Test (ppm) | | | | | | | | 58 | 1099 |

| | Sample No. | | | | | | | |
|---|---|---|---|---|---|---|---|---|
| | 44 | 44' | 56 | 60 | 61 | 69 | 73 | 75 |
| Sample Age at Time of Test (days) | 43 | 6 | 35 | 35 | 35 | 22 | 22 | 15 |
| Calculated Original Concentration of Chlorite (ppm) | 11250 | 11250 | 11250 | 11250 | 11250 | 90000 | 90000 | 11250 |
| Calculated Original Concentration of Iodide (ppm) | | | | | | 40000 | 40000 | 5000 |
| Calculated Original Concentration of Activator (ppm) | 10000 | 10000 | 10000 | 1784 | 3567 | | | |
| Chloride Concentration at Time of Test (ppm) | 452 | 1357 | 1568 | 194 | 3543 | 18291 | 19868 | 172 |
| Chlorite Concentration at Time of Test (ppm) | 8019 | 7223 | 5857 | 8984 | 1498 | 137140 | 153751 | 8536 |
| Chlorite Remaining at Time of Test (%) | 71 | 64 | 52 | 80 | 13 | 152 | 171 | 76 |
| Chlorate Concentration at Time of Test (ppm) | 87 | 91 | 76 | 51 | 85 | 976 | 1043 | 47 |

TABLE 2-continued

| | | | | | | | | |
|---|---|---|---|---|---|---|---|---|
| Iodide Concentration at Time of Test (ppm) | | | | | | 36130 | 41256 | 4341 |
| Iodide Remaining at Time of Test (%) | | | | | | 90 | 103 | 87 |
| Iodate Concentration at Time of Test (ppm) | | | | | | 27406 | 14886 | 241 |
| Thiosulfate Concentration at Time of Test (ppm) | | | | 252 | 0 | | | |
| Thiosulfate Remaining at Time of Test (%) | | | | 14 | 0 | | | |
| Sulfite Concentration at Time of Test (ppm) | 0 | 0 | 0 | | | | | |
| Sulfite Remaining at Time of Test (%) | 0 | 0 | 0 | | | | | |
| Sulfate Concentration at Time of Test (ppm) | 9042 | 10450 | 18513 | 413 | 3442 | | | |

TABLE 3

| | Sample No. | | | | | | | | | | | |
|---|---|---|---|---|---|---|---|---|---|---|---|---|
| | 1 | 3 | 7 | 7' | 11 | 12 | 12' | 13 | 14 | 18 | 19 | 20 |
| Sample Age at Time of Test (days) | 245 | 245 | 151 | 199 | 151 | 151 | 18 | 151 | 151 | 127 | 127 | 127 |
| Absorbance at 1 min | 1.057 | 0.03 | 0.018 | 0.643 | 0.014 | 1.692 | 0.667 | 0.026 | 0.015 | 0.011 | 1.454 | 1.201 |
| Concentration of $ClO_2$ (ppm) at 1 min | 57 | 2 | 1 | 35 | 1 | 91 | 36 | 1 | 1 | 1 | 79 | 65 |
| % yield at 1 min | 42 | 1 | 1 | 26 | 1 | 68 | 27 | 1 | 1 | 0 | 58 | 48 |
| Absorbance at 10 min | 1.019 | 0.083 | 0.049 | 0.604 | 0.031 | 1.701 | 0.622 | 0.061 | 0.043 | 0.026 | 1.341 | 1.158 |
| Concentration of $ClO_2$ (ppm) at 10 min | 55 | 4 | 3 | 33 | 2 | 92 | 34 | 3 | 2 | 1 | 72 | 63 |
| % yield at 10 min | 41 | 3 | 2 | 24 | 1 | 68 | 25 | 2 | 2 | 1 | 54 | 47 |
| Absorbance at 30 min | 0.95 | 0.137 | 0.089 | 0.57 | 0.057 | 1.56 | 0.577 | 0.112 | 0.089 | 0.05 | 1.254 | 1.076 |
| Concentration of $ClO_2$ (ppm) at 30 min | 51 | 7 | 5 | 31 | 3 | 84 | 31 | 6 | 5 | 3 | 68 | 58 |
| % yield at 30 min | 38 | 6 | 4 | 23 | 2 | 63 | 23 | 5 | 4 | 2 | 50 | 43 |

| | Sample No. | | | | | | | | | | | |
|---|---|---|---|---|---|---|---|---|---|---|---|---|
| | 21 | 23 | 24 | 25 | 27 | 28 | 29 | 30 | 31 | 34 | 35 | 36 |
| Sample Age at Time of Test (days) | 127 | 127 | 127 | 127 | 127 | 127 | 72 | 72 | 72 | 70 | 70 | 70 |
| Absorbance at 1 min | 1.143 | 0.132 | 1.466 | 0.979 | 1.255 | 1.024 | 1.182 | 0.726 | 0.13 | 1.198 | 0.039 | 0.524 |
| Concentration of $ClO_2$ (ppm) at 1 min | 62 | 7 | 79 | 53 | 68 | 55 | 64 | 39 | 7 | 65 | 2 | 28 |
| % yield at 1 min | 46 | 5 | 59 | 39 | 50 | 41 | 48 | 29 | 5 | 48 | 2 | 21 |
| Absorbance at 10 min | 1.113 | 0.122 | 1.389 | 0.864 | 1.195 | 0.949 | 1.152 | 0.718 | 0.354 | 1.124 | 0.287 | 0.508 |
| Concentration of $ClO_2$ (ppm) at 10 min | 60 | 7 | 75 | 47 | 65 | 51 | 62 | 39 | 19 | 61 | 15 | 27 |
| % yield at 10 min | 45 | 5 | 56 | 35 | 48 | 38 | 46 | 29 | 14 | 45 | 12 | 20 |
| Absorbance at 30 min | 1.029 | 0.106 | 1.297 | 0.823 | 1.124 | 0.887 | 1.083 | 0.675 | 0.734 | 1.057 | 1.331 | 0.479 |
| Concentration of $ClO_2$ (ppm) at 30 min | 56 | 6 | 70 | 44 | 61 | 48 | 58 | 36 | 40 | 57 | 72 | 26 |
| % yield at 30 min | 41 | 4 | 52 | 33 | 45 | 36 | 44 | 27 | 29 | 42 | 53 | 19 |

| | Sample No. | | | | | | | | | | | |
|---|---|---|---|---|---|---|---|---|---|---|---|---|
| | 37 | 38 | 41 | 41' | 42 | 44 | 45 | 47 | 48 | 48' | 49 | 50 |
| Sample Age at Time of Test (days) | 70 | 70 | 70 | 37 | 65 | 65 | 65 | 52 | 52 | 6 | 52 | 52 |
| Absorbance at 1 min | 1.378 | 1.467 | 0.034 | 0.026 | 0.027 | 0.059 | 0.08 | 0.543 | 0.047 | 0.063 | 0.003 | 1.068 |
| Concentration of $ClO_2$ (ppm) at 1 min | 74 | 79 | 2 | 1 | 1 | 3 | 4 | 29 | 3 | 3 | 0 | 58 |
| % yield at 1 min | 55 | 59 | 1 | 1 | 1 | 2 | 3 | 22 | 2 | 3 | 0 | 43 |
| Absorbance at 10 min | 1.309 | 1.351 | 0.049 | 0.064 | 0.055 | 0.059 | 0.067 | 0.533 | 0.085 | 0.127 | 0.003 | 1.052 |
| Concentration of $ClO_2$ (ppm) at 10 min | 71 | 73 | 3 | 3 | 3 | 3 | 4 | 29 | 5 | 7 | 0 | 57 |
| % yield at 10 min | 53 | 54 | 2 | 3 | 2 | 2 | 3 | 21 | 3 | 5 | 0 | 42 |
| Absorbance at 30 min | 1.225 | 1.256 | 0.071 | 0.106 | 0.089 | 0.084 | 0.044 | 0.532 | 0.132 | 0.191 | 0.004 | 0.975 |
| Concentration of $ClO_2$ (ppm) at 30 min | 66 | 68 | 4 | 6 | 5 | 5 | 2 | 29 | 7 | 10 | 0 | 53 |
| % yield at 30 min | 49 | 50 | 3 | 4 | 4 | 3 | 2 | 21 | 5 | 8 | 0 | 39 |

TABLE 3-continued

| | Sample No. | | | | | | | | | | | |
|---|---|---|---|---|---|---|---|---|---|---|---|---|
| | 52 | 53 | 54 | 56 | 56' | 57 | 58 | 59 | 60 | 61 | 62 | 63 |
| Sample Age at Time of Test (days) | 52 | 52 | 52 | 52 | 6 | 52 | 52 | 52 | 52 | 52 | 43 | 43 |
| Absorbance at 1 min | 0.042 | 0.012 | 0.018 | 0.01 | 0.016 | 0.134 | 0.019 | 0.031 | 0.317 | 0.005 | 0.024 | 0.001 |
| Concentration of $ClO_2$ (ppm) at 1 min | 2 | 1 | 1 | 1 | 1 | 7 | 1 | 2 | 17 | 0 | 1 | 0 |
| % yield at 1 min | 2 | 0 | 1 | 0 | 1 | 5 | 1 | 1 | 13 | 0 | 1 | 0 |
| Absorbance at 10 min | 0.073 | 0.027 | 0.042 | 0.019 | 0.039 | 0.129 | 0.043 | 0.06 | 0.314 | 0.007 | 0.07 | 0.006 |
| Concentration of $ClO_2$ (ppm) at 10 min | 4 | 1 | 2 | 1 | 2 | 7 | 2 | 3 | 17 | 0 | 4 | 0 |
| % yield at 10 min | 3 | 1 | 2 | 1 | 2 | 5 | 2 | 2 | 13 | 0 | 3 | 0 |
| Absorbance at 30 min | 0.126 | 0.043 | 0.075 | 0.034 | 0.068 | 0.139 | 0.082 | 0.106 | 0.313 | 0.004 | 0.12 | 0.003 |
| Concentration of $ClO_2$ (ppm) at 30 min | 7 | 2 | 4 | 2 | 4 | 8 | 4 | 6 | 17 | 0 | 6 | 0 |
| % yield at 30 min | 5 | 2 | 3 | 1 | 3 | 6 | 3 | 4 | 13 | 0 | 5 | 0 |

| | Sample No. | | | | | | | | | | | |
|---|---|---|---|---|---|---|---|---|---|---|---|---|
| | 64 | 65 | 66 | 67 | 68 | 69 | 70 | 71 | 72 | 73 | 74 | 75 |
| Sample Age at Time of Test (days) | 43 | 38 | 38 | 38 | 38 | 38 | 38 | 38 | 38 | 38 | 31 | 31 |
| Absorbance at 1 min | 0.022 | 0.01 | 0.625 | 1.48 | 0.016 | 1.441 | 1.922 | 1.602 | 1.135 | 1.159 | 0.038 | 1.097 |
| Concentration of $ClO_2$ (ppm) at 1 min | 1 | 1 | 34 | 80 | 1 | 78 | 104 | 87 | 61 | 63 | 2 | 59 |
| % yield at 1 min | 1 | 0 | 25 | 59 | 1 | 58 | 77 | 64 | 46 | 47 | 2 | 44 |
| Absorbance at 10 min | 0.038 | 0.024 | 0.597 | 1.421 | 0.026 | 1.406 | 1.843 | 1.561 | 1.157 | 1.134 | 0.066 | 1.061 |
| Concentration of $ClO_2$ (ppm) at 10 min | 2 | 1 | 32 | 77 | 1 | 76 | 100 | 84 | 62 | 61 | 4 | 57 |
| % yield at 10 min | 2 | 1 | 24 | 57 | 1 | 57 | 74 | 63 | 47 | 46 | 3 | 43 |
| Absorbance at 30 min | 0.056 | 0.036 | 0.559 | 1.318 | 0.051 | 1.36 | 1.75 | 1.495 | 1.096 | 1.111 | 0.113 | 0.989 |
| Concentration of $ClO_2$ (ppm) at 30 min | 3 | 2 | 30 | 71 | 3 | 73 | 95 | 81 | 59 | 60 | 6 | 53 |
| % yield at 30 min | 2 | 1 | 22 | 53 | 2 | 55 | 70 | 60 | 44 | 45 | 5 | 40 |

| | Sample No. | | | | | | | | | | | |
|---|---|---|---|---|---|---|---|---|---|---|---|---|
| | 76' | 77' | 78 | 79 | 80 | 82 | 83 | 84 | 85 | 86 | 87 | 88 |
| Sample Age at Time of Test (days) | 6 | 6 | 31 | 31 | 31 | 4 | 4 | 4 | 4 | 4 | 4 | 4 |
| Absorbance at 1 min | 0.061 | 0.089 | 0.036 | 0.026 | 0.028 | 0.897 | 0.818 | 1.199 | 1.28 | 0.307 | 0.454 | 0.78 |
| Concentration of $ClO_2$ (ppm) at 1 min | 3 | 5 | 2 | 1 | 2 | 48 | 44 | 65 | 69 | 17 | 25 | 42 |
| % yield at 1 min | 2 | 4 | 1 | 1 | 1 | 36 | 33 | 48 | 51 | 12 | 18 | 31 |
| Absorbance at 10 min | 0.134 | 0.185 | 0.082 | 0.071 | 0.061 | 0.863 | 0.614 | 1.12 | 1.23 | 0.312 | 0.415 | 0.756 |
| Concentration of $ClO_2$ (ppm) at 10 min | 7 | 10 | 4 | 4 | 3 | 47 | 33 | 60 | 66 | 17 | 22 | 41 |
| % yield at 10 min | 5 | 7 | 3 | 3 | 2 | 35 | 25 | 45 | 49 | 13 | 17 | 30 |
| Absorbance at 30 min | 0.233 | 0.316 | 0.14 | 0.126 | 0.123 | 0.823 | 0.522 | 1.046 | 1.142 | 0.326 | 0.402 | 0.711 |
| Concentration of $ClO_2$ (ppm) at 30 min | 13 | 17 | 8 | 7 | 7 | 44 | 28 | 56 | 62 | 18 | 22 | 38 |
| % yield at 30 min | 9 | 13 | 6 | 5 | 5 | 33 | 21 | 42 | 46 | 13 | 16 | 29 |

| | Sample No. | | | | | | | | | | | |
|---|---|---|---|---|---|---|---|---|---|---|---|---|
| | 89 | 90 | 91 | 92 | 93 | 94 | 95 | 96 | 97 | 98 | 99 | 100 |
| Sample Age at Time of Test (days) | 4 | 4 | 4 | 4 | 4 | 4 | 4 | 4 | 4 | 4 | 4 | 4 |
| Absorbance at 1 min | 1.298 | 1.6 | 1.196 | 0.293 | 0.125 | 0.307 | 0.421 | 0.532 | 0.517 | 0.116 | 0.003 | 0.004 |
| Concentration of $ClO_2$ (ppm) at 1 min | 70 | 86 | 65 | 16 | 7 | 17 | 23 | 29 | 28 | 6 | 0 | 0 |
| % yield at 1 min | 52 | 64 | 48 | 12 | 5 | 12 | 17 | 21 | 21 | 5 | 0 | 0 |
| Absorbance at 10 min | 1.25 | 1.557 | 1.147 | 0.285 | 0.112 | 0.31 | 0.407 | 0.521 | 0.51 | 0.11 | 0.003 | 0.004 |
| Concentration of $ClO_2$ (ppm) at 10 min | 68 | 84 | 62 | 15 | 6 | 17 | 22 | 28 | 28 | 6 | 0 | 0 |
| % yield at 10 min | 50 | 63 | 46 | 11 | 5 | 12 | 16 | 21 | 20 | 4 | 0 | 0 |
| Absorbance at 30 min | 1.109 | 1.44 | 1.437 | 0.258 | 0.089 | 0.305 | 0.33 | 0.49 | 0.475 | 0.099 | 0 | 0.04 |
| Concentration of $ClO_2$ (ppm) at 30 min | 60 | 78 | 78 | 14 | 5 | 16 | 18 | 26 | 26 | 5 | 0 | 2 |
| % yield at 30 min | 45 | 58 | 58 | 10 | 4 | 12 | 13 | 20 | 19 | 4 | 0 | 2 |

| | Sample No. | | | | | | | | | | | |
|---|---|---|---|---|---|---|---|---|---|---|---|---|
| | 101 | 102 | 103 | 104 | 105 | 106 | 107 | 108 | 109 | 110 | 111 | 112 |
| Sample Age at Time of Test (days) | 3 | 2 | 2 | 2 | 2 | 5 | 5 | 5 | 5 | 5 | 4 | 4 |
| Absorbance at 1 min | 0.511 | 0.052 | 0.044 | 0.076 | 0.074 | 0.033 | 0.044 | 0.048 | 0.055 | 0.074 | 0.06 | 0.065 |
| Concentration of $ClO_2$ (ppm) at 1 min | 28 | 3 | 2 | 4 | 4 | 2 | 2 | 3 | 3 | 4 | 3 | 4 |

TABLE 3-continued

| | | | | | | | | | | | | |
|---|---|---|---|---|---|---|---|---|---|---|---|---|
| % yield at 1 min | 21 | 2 | 2 | 3 | 3 | 1 | 2 | 2 | 2 | 3 | 2 | 3 |
| Absorbance at 10 min | 0.499 | 0.081 | 0.075 | 0.088 | 0.086 | 0.091 | 0.105 | 0.11 | 0.109 | 0.124 | 0.087 | 0.091 |
| Concentration of $ClO_2$ (ppm) at 10 min | 27 | 4 | 4 | 5 | 5 | 5 | 6 | 6 | 6 | 7 | 5 | 5 |
| % yield at 10 min | 20 | 3 | 3 | 4 | 3 | 4 | 4 | 4 | 4 | 5 | 3 | 4 |
| Absorbance at 30 min | 0.47 | 0.125 | 0.122 | 0.116 | 0.106 | 0.151 | 0.169 | 0.174 | 0.165 | 0.174 | 0.127 | 0.13 |
| Concentration of $ClO_2$ (ppm) at 30 min | 25 | 7 | 7 | 6 | 6 | 8 | 9 | 9 | 9 | 9 | 7 | 7 |
| % yield at 30 min | 19 | 5 | 5 | 5 | 4 | 6 | 7 | 7 | 7 | 7 | 5 | 5 |

| | Sample No. | | | | | | | | | | | |
|---|---|---|---|---|---|---|---|---|---|---|---|---|
| | 113 | 114 | 115 | 116 | 117 | 118 | 119 | 120 | 121 | 122 | 123 | 124 |
| Sample Age at Time of Test (days) | 4 | 4 | 4 | 0 | 1 | 1 | 1 | 1 | 1 | 1 | 1 | 1 |
| Absorbance at 1 min | 0.05 | 0.041 | 0.034 | 0.028 | 0.119 | 0.067 | 0.066 | 0.062 | 0.057 | 0.846 | 0.21 | 0.06 |
| Concentration of $ClO_2$ (ppm) at 1 min | 3 | 2 | 2 | 2 | 6 | 4 | 4 | 3 | 3 | 46 | 11 | 3 |
| % yield at 1 min | 2 | 2 | 1 | 1 | 5 | 3 | 3 | 2 | 2 | 34 | 8 | 2 |
| Absorbance at 10 min | 0.09 | 0.088 | 0.085 | 0.073 | | | | | | | | |
| Concentration of $ClO_2$ (ppm) at 10 min | 5 | 5 | 5 | 4 | 0 | 0 | 0 | 0 | 0 | 0 | 0 | 0 |
| % yield at 10 min | 4 | 4 | 3 | 3 | 0 | 0 | 0 | 0 | 0 | 0 | 0 | 0 |
| Absorbance at 30 min | 0.143 | 0.145 | 0.143 | 0.133 | | | | | | | | |
| Concentration of $ClO_2$ (ppm) at 30 min | 8 | 8 | 8 | 7 | 0 | 0 | 0 | 0 | 0 | 0 | 0 | 0 |
| % yield at 30 min | 6 | 6 | 6 | 5 | 0 | 0 | 0 | 0 | 0 | 0 | 0 | 0 |

| | Sample No. | | | | | | | | | |
|---|---|---|---|---|---|---|---|---|---|---|
| | 125 | 126 | 127 | 128 | 129 | 130 | 131 | 132 | 133 | 134 |
| Sample Age at Time of Test (days) | 1 | 1 | 0 | 0 | 0 | 0 | 0 | 0 | 0 | 0 |
| Absorbance at 1 min | 0.162 | 0.309 | 0.029 | 0.06 | 0.04 | 0.072 | 0.023 | 0.031 | 0.047 | 0.028 |
| Concentration of $ClO_2$ (ppm) at 1 min | 9 | 17 | 2 | 3 | 2 | 4 | 1 | 2 | 3 | 2 |
| % yield at 1 min | 7 | 12 | 1 | 2 | 2 | 3 | 1 | 1 | 2 | 1 |
| Absorbance at 10 min | | | 0.07 | 0.119 | 0.082 | 0.132 | 0.051 | 0.065 | 0.093 | 0.055 |
| Concentration of $ClO_2$ (ppm) at 10 min | 0 | 0 | 4 | 6 | 4 | 7 | 3 | 4 | 5 | 3 |
| % yield at 10 min | 0 | 0 | 3 | 5 | 3 | 5 | 2 | 3 | 4 | 2 |
| Absorbance at 30 min | | | 0.123 | 0.189 | 0.139 | 0.202 | 0.103 | 0.119 | 0.154 | 0.101 |
| Concentration of $ClO_2$ (ppm) at 30 min | 0 | 0 | 7 | 10 | 8 | 11 | 6 | 6 | 8 | 5 |
| % yield at 30 min | 0 | 0 | 5 | 8 | 6 | 8 | 4 | 5 | 6 | 4 |

What is claimed is:

1. An aqueous composition for producing chlorine dioxide upon contact with an acid, the composition comprising:
   a chlorite ion source comprising a chlorite; and
   water,
   wherein the pH of the aqueous composition is at least 11.5, the composition produces chlorine dioxide upon contact with an acid, and the molar ratio of the chlorite to the thiosulfate in the composition is from 20:1 to 2:1.

2. The composition according to claim 1, further comprising a separate source of alkalinity.

3. The composition according to claim 2, wherein the separate source of alkalinity comprises at least one selected from the group consisting of hydroxides, carbonates, silicates, and amines.

4. The composition according to claim 1, wherein the composition produces chlorine dioxide at a concentration of 0.01 to 100 ppm when the composition contacts the acid.

5. The composition according to claim 1, wherein the molar ratio of the chlorite to the thiosulfate in the composition is from 20:1 to 4:1.

6. The composition according to claim 1, wherein the chlorite is selected from sodium chlorite and calcium chlorite and the thiosulfate is selected from sodium thiosulfate and potassium thiosulfate.

7. The composition according to claim 1, wherein the chlorite is sodium chlorite and the thiosulfate is sodium thiosulfate.

8. The composition according to claim 1, consisting of the thiosulfate, the chlorite, the water, a separate source of alkalinity, and optionally, a corrosion inhibitor selected from aminotris(methylenephosphonic acid) (ATMP), 1-hydroxyethane 1,1-diphosphonic acid (HEDP), and 2-phosphonobutane-1,2,4-tricarboxylic acid (PBTC).

9. A clean-in-place system comprising a tank comprising the composition according to claim 1 and a separate source of the acid.

10. An aqueous composition for producing chlorine dioxide upon contact with an acid, the composition comprising:
    a chlorite ion source comprising a chlorite; and
    water,
    wherein the pH of the aqueous composition is at least 10.39, the composition produces chlorine dioxide upon contact with an acid, and the molar ratio of the chlorite to the iodide in the composition is from 40:1 to 1:1.

11. The composition according to claim 10, wherein the molar ratio of the chlorite to the iodide in the composition is from 40:1 to 2:1.

12. The composition according to claim 10, wherein the chlorite is selected from sodium chlorite and calcium chlorite and the iodide is selected from sodium iodide and potassium iodide.

13. The composition according to claim 10, wherein the chlorite is sodium chlorite and the iodide is potassium thiosulfate.

14. The composition according to claim 10, consisting of the iodide, the chlorite, the water, a separate source of alkalinity, and optionally, a corrosion inhibitor selected from aminotris(methylenephosphonic acid) (ATMP), 1-hydroxyethane 1,1-diphosphonic acid (HEDP), and 2-phosphonobutane-1,2,4-tricarboxylic acid (PBTC).

15. A clean-in-place system comprising a tank comprising the composition according to claim 10 and a separate source of the acid.

16. A method of producing chlorine dioxide comprising:
    contacting the aqueous composition according to claim 1 with the acid.

17. The method according to claim 16, further comprising applying chlorine dioxide, produced by contacting the aqueous composition with the acid, in at least one process selected from the group consisting of a disinfection process, a sanitization process, a cleaning process, and a sterilization process.

18. The method according to claim 16, wherein the acid comprises at least one selected from the group consisting of an acidic biocide, an acidic detergent, an acidic descaler, an acidic sanitizer, and an acidic disinfectant.

19. The method according to claim 16, wherein the acid is in the form of an acidic foam.

20. The method according to claim 16, wherein a concentration of the chlorine dioxide produced is 0.01 to 100 ppm.

* * * * *

UNITED STATES PATENT AND TRADEMARK OFFICE
CERTIFICATE OF CORRECTION

PATENT NO. : 10,472,237 B2  
APPLICATION NO. : 15/735230  
DATED : November 12, 2019  
INVENTOR(S) : Henry von Rege et al.

Page 1 of 1

It is certified that error appears in the above-identified patent and that said Letters Patent is hereby corrected as shown below:

In the Claims

Claim 1, Column 83, Lines 41-43:
Delete the phrase "the composition comprising: a chlorite ion source comprising a chlorite; and water," and replace with --the composition comprising: a thiosulfate; a chlorite ion source comprising a chlorite; and water,--.

Claim 10, Column 84, Lines 50-51:
Delete the phrase "the composition comprising: a chlorite ion source comprising a chlorite; and water," and replace with --the composition comprising: an iodide; a chlorite ion source comprising a chlorite; and water,--.

Signed and Sealed this
Twenty-fourth Day of December, 2019

Andrei Iancu
*Director of the United States Patent and Trademark Office*